(12) United States Patent
Scheurich et al.

(10) Patent No.: US 10,125,214 B2
(45) Date of Patent: Nov. 13, 2018

(54) MATERIALS FOR ELECTRONIC DEVICES

(75) Inventors: René Peter Scheurich, Gross-Zimmern (DE); Junyou Pan, Frankfurt am Main (DE); Frank Egon Meyer, Winchester (GB); Niels Schulte, Kelkheim (DE); Rémi Manouk Anèmian, Seoul (KR); Susanne Heun, Bad Soden (DE); Thomas Eberle, Landau (DE); Aurélie Ludemann, Frankfurt am Main (DE); Herwig Buchholz, Frankfurt am Main (DE); Wolfgang Hierse, Gross-Zimmern (DE)

(73) Assignee: Merck Patent GmbH (DE)

( * ) Notice: Subject to any disclaimer, the term of this patent is extended or adjusted under 35 U.S.C. 154(b) by 1123 days.

(21) Appl. No.: 13/386,439

(22) PCT Filed: Jun. 24, 2010

(86) PCT No.: PCT/EP2010/003881
§ 371 (c)(1),
(2), (4) Date: Feb. 22, 2012

(87) PCT Pub. No.: WO2011/009522
PCT Pub. Date: Jan. 27, 2011

(65) Prior Publication Data
US 2012/0142855 A1 Jun. 7, 2012

(30) Foreign Application Priority Data
Jul. 22, 2009 (DE) .................. 10 2009 034 194

(51) Int. Cl.
| | | |
|---|---|---|
| C07C 25/22 | (2006.01) | |
| C08G 61/12 | (2006.01) | |
| C07C 211/31 | (2006.01) | |
| C08G 61/02 | (2006.01) | |
| C09D 165/00 | (2006.01) | |
| H01L 51/00 | (2006.01) | |
| H01L 51/50 | (2006.01) | |

(52) U.S. Cl.
CPC .............. *C08G 61/12* (2013.01); *C07C 25/22* (2013.01); *C07C 211/31* (2013.01); *C08G 61/02* (2013.01); *C08G 61/126* (2013.01); *C09D 165/00* (2013.01); *H01L 51/0003* (2013.01); *H01L 51/0035* (2013.01); *H01L 51/0039* (2013.01); *H01L 51/5012* (2013.01); *C07C 2603/52* (2017.05); *C08G 2261/143* (2013.01); *C08G 2261/146* (2013.01); *C08G 2261/1424* (2013.01); *C08G 2261/316* (2013.01); *C08G 2261/3142* (2013.01); *C08G 2261/411* (2013.01); *C08G 2261/5222* (2013.01); *Y02E 10/549* (2013.01)

(58) Field of Classification Search
CPC .................................................... C07C 25/22

USPC ......................................................... 524/609
See application file for complete search history.

(56) References Cited

U.S. PATENT DOCUMENTS

| | | |
|---|---|---|
| 2003/0062509 A1 | 4/2003 | Heeney et al. |
| 2004/0135131 A1 | 7/2004 | Treacher et al. |
| 2006/0046092 A1 | 3/2006 | Towns et al. |
| 2006/0228576 A1 | 10/2006 | Burroughes et al. |
| 2007/0252139 A1* | 11/2007 | Mckiernan ............ C08G 61/02 257/40 |
| 2008/0145708 A1 | 6/2008 | Heil et al. |
| 2008/0149878 A1 | 6/2008 | Kirsch et al. |
| 2008/0220285 A1 | 9/2008 | Vestweber et al. |
| 2009/0036623 A1 | 2/2009 | Tsuda et al. |
| 2010/0171102 A1 | 7/2010 | Le et al. |
| 2011/0068329 A1 | 3/2011 | Buchholz et al. |
| 2011/0095283 A1* | 4/2011 | Buchholz et al. ............... 257/40 |
| 2012/0056168 A1 | 3/2012 | Ie et al. |

FOREIGN PATENT DOCUMENTS

| | | | |
|---|---|---|---|
| EP | 1279689 A2 | 1/2003 | |
| JP | H03244631 A | 10/1991 | |
| JP | 2003176338 A | 6/2003 | |
| JP | 2004536896 A | 12/2004 | |
| JP | 2005314452 A | 11/2005 | |
| JP | 2006505647 A | 2/2006 | |
| JP | 2006176755 | 7/2006 | |
| JP | 2006517595 A | 7/2006 | |
| JP | 2008255097 A | 10/2008 | |
| JP | 2010209264 A | 9/2010 | |
| WO | WO 0053656 A1 * | 9/2000 | ............ C08G 61/02 |
| WO | WO-2002/077060 A1 | 10/2002 | |
| WO | WO-2004/041901 A1 | 5/2004 | |
| WO | WO-2004/041902 A2 | 5/2004 | |
| WO | WO 2004041901 A1 * | 5/2004 | ............ C08G 61/00 |
| WO | WO-2004/113412 A2 | 12/2004 | |
| WO | WO-2005/073338 A2 | 8/2005 | |

(Continued)

OTHER PUBLICATIONS

English machine translation of Konishi et al. (WO 2005/100437), generated May 21, 2015.*

(Continued)

*Primary Examiner* — Michael F Pepitone
(74) *Attorney, Agent, or Firm* — Drinker Biddle & Reath LLP

(57) ABSTRACT

The present invention relates to polymers comprising structural units having partially fluorinated substituents, to mixtures and formulations comprising the polymers according to the invention, to a process for the preparation of the polymers according to the invention, and to the use of the polymers according to the invention as functional materials in electronic devices.

14 Claims, No Drawings

(56) References Cited

FOREIGN PATENT DOCUMENTS

| WO | WO 2005100437 A1 * | 10/2005 |
| WO | WO-2006/072401 A1 | 7/2006 |
| WO | WO-2006/108497 A1 | 10/2006 |
| WO | WO-2006/122630 A1 | 11/2006 |
| WO | WO-2006126439 A1 | 11/2006 |
| WO | WO-2009/053088 A1 | 4/2009 |
| WO | WO-2009053088 A1 | 4/2009 |
| WO | WO-2009053089 A1 | 4/2009 |
| WO | WO-2010025802 A1 | 3/2010 |

OTHER PUBLICATIONS

Kameshima, H.; Nemoto, N.; Endo, T. J. Polym. Sci. A Polym. Chem. 2001, 39, 3143. John wiley & Sons, Inc.*

Lee, J.-K.; Fong, H., H.; Zakhidov, A., A.; McCluskey, G., E.; Taylor, P., G.; Holmes, A., B.; Malliaras, G.; G.; Ober, C., K. PMSE Preprints 2009, 100, 504. American Chemical Society.*

PMSE Preprints cover page, vol. 100, Spring 2009; Mar. 22-26, 2009. American Chemical Society.*

International Search Report for PCT/EP2010/003881 dated Jul. 13, 2011.

Kotaka, et al., "Facile Synthesis and Luminescence Property of a Functional Polyfluorene Having a Fluoroalkyl Side Chain", ITE Letters, vol. 6, No. 6, (2005), pp. 49-51.

Darmanin, et al., "Synthesis and Properties of Perfluorinated Conjugated Polymers Based on Polyethylenedioxythiophene, Polypyrrole, and Polyfluorene. Toward Surfaces with Special Wettabilities", Langmuir, vol. 24, (2008), pp. 9739-9746.

Amara, et al., "Conjugated Polymers with Geminal Trifluoromethyl Substituents Derived from Hexafluoroacetone", Macromolecules, vol. 39, (2006), pp. 5753-5759.

Lee et al. "Synthesis of Semiperfluoralkyl Polyfluorenes for Orthogonal Processing in Hydrofluorether Solvents" Abstract of papers, $237^{th}$ ACS National Meeting, Salt Lake City, Ut Mar. 22-26, 2009 conference Abstract CAPLUS Database No. 1152.

Japanese Office Action dated Dec. 3, 2013 for JP 2012-516541.

* cited by examiner

MATERIALS FOR ELECTRONIC DEVICES

The present invention relates to polymers comprising structural units having partially fluorinated side chains, and to the use thereof in organic electronic devices.

Compounds like the polymers according to the invention are being developed for a number of different applications which can be ascribed to the electronics industry in the broadest sense. The structure of organic electro-luminescent devices (OLEDs) in which these organic semiconductors are preferably employed, inter alia, as functional materials is described, for example, in U.S. Pat. Nos. 4,539,507, 5,151,629, EP 0676461 and WO 98/27136.

The prior art discloses various polymeric materials which are suitable for use in organic electroluminescent devices. Thus, for example, compounds based on monomer units, such as spirobifluorene, fluorene, indenofluorene, phenanthrene or dihydrophenanthrene, are disclosed in WO 04/041901, WO 04/113412 and WO 05/014689.

There continues to be a demand for novel materials for use in organic electronic devices, in particular with respect to an improvement in the devices in the following points:
1. Compounds having a low LUMO (lowest unoccupied molecular orbital) are required for easier electron injection and thus for a reduction in the operating voltage. A reduction in the operating voltage results in an improvement in the power efficiency, which is of major importance, in particular, for mobile applications.
2. Materials having improved differentiability with respect to solubility and wetting properties are required in order to be able to achieve multilayered systems.
3. The aim was to further increase the lifetime and efficiency of organic electroluminescent devices, in particular in the case of blue-emitting systems and with respect to high-quality applications.

In summary, the present invention is based on the object of providing novel functional materials for electronic devices, preferably those which enable improved electron injection and/or have modified solubility properties which simplify the application of multilayered structures.

It has now been found that compounds comprising one or more structural elements having partially fluorinated substituents $R_F$ of the formula (I) can successfully be employed as functional materials in electronic devices, preferably organic electroluminescent devices.

The introduction of partially fluorinated side chains, as described in the present application, preferably facilitates a lowering of the LUMO orbital of the compounds and thus a lowering of the electron-injection barrier, causing a reduction in the operating voltage of the electronic devices.

Furthermore, the introduction of partially fluorinated side chains, as described in the present application, preferably facilitates modification of the solubility properties, which simplifies the construction of electronic devices comprising a plurality of layers of functional materials.

The present application thus relates to polymers comprising one or more structural elements of the formula (I),

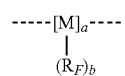

formula (I)

where
M on each occurrence, identically or differently, represents an aromatic, heteroaromatic or aliphatically bridged aromatic ring system, which may optionally be substituted by one or more radicals $R^1$, where the substituents $R_F$ and $R^1$ defined below may be identical or different on each occurrence, with the proviso that the following applies to the indices a and b mentioned above:
$1 \leq a \leq 10{,}000$
$1 \leq b \leq 10$
and the dashed lines represent bonds to adjacent structural units, where, in addition, more than two such bonds may be present.

Furthermore, the compounds according to the invention may additionally comprise further identical or different structural elements M which are not substituted by $R_F$, with the proviso that the sum of the structural units M in the polymers according to the invention is between 2 and 10,000.

Furthermore, for $R_F$ and $R^1$, $R_F$ represents a fluorinated organic substituent having 1 to 60 C atoms, which may be saturated or unsaturated, linear, cyclic or branched and in which, in addition, one or more adjacent or non-adjacent $CH_2$ groups may be replaced by O, S, Se, Te, $Si(R^2)_2$, $Ge(R^2)_2$, $BR^2$, $NR^2$, $PR^2$, CO, C=S, C=Se, C=$NR^2$, $PO(R^2)$, $PS(R^2)$, $R^2C$=$CR^2$, C≡C, SO, $SO_2$, COO, O(CO)O or $CONR^2$, with the proviso that $R_F$ is not fully fluorinated, i.e. the carbon backbone of the radical $R_F$ is substituted by a substituent other than F at at least one free position, and that two or more radicals $R_F$ which are bonded to one group M or to two or more different adjacent or non-adjacent groups M can form an aliphatic, unsaturated or aromatic ring system, and $R^1$ on each occurrence, identically or differently, represents H, F or an aliphatic, aromatic and/or heteroaromatic hydrocarbon radical having 1 to 20 C atoms, in which, in addition, one or more H atoms may be replaced by F and in which, in addition, one or more adjacent or non-adjacent $CH_2$ groups may be replaced by O, S, Se, Te, $Si(R^2)_2$, $Ge(R^2)_2$, $BR^2$, $NR^2$, $PR^2$, CO, C=S, C=Se, C=$NR^2$, $PO(R^2)$, $PS(R^2)$, $R^2C$=$CR^2$, C≡C, SO, $SO_2$, COO, O(CO)O or $CONR^2$, with the proviso that two or more substituents $R^1$ which are bonded to one group M or to two or more different adjacent or non-adjacent groups M can form an aliphatic, unsaturated or aromatic ring system, and $R^2$ on each occurrence, identically or differently, represents H, F or an aliphatic, aromatic and/or heteroaromatic hydrocarbon radical having 1 to 20 C atoms, in which one or more H atoms may be replaced by F.

Monomer building blocks having fully fluorinated side chains and polymeric materials comprising structural elements of this type for use in organic electroluminescent devices are known from the literature (T. Swager et al., *Macromolecules* 2006, 39 (17), 5753 and WO 05/073338). However, the use of partially fluorinated side chains in the functional materials in question is not mentioned in the corresponding publications.

Compounds containing partially fluorinated substituents were hitherto known from the area of surfactants, where they are employed owing to their good biodegradability and surface-active action, as described, for example, in WO 2006/072401.

The polymers according to the invention preferably comprise 2 to 10,000 recurring units, where the term "polymer" in the present application is intended to encompass both polymers and also dendrimers and oligomers. The oligomeric compounds according to the invention preferably have 2 to 9 recurring units. Preferred polymers and dendrimers according to the invention comprise structural elements of the formula (I) with a total of 10 to 10,000 monomer units and a molecular weight of 1000 to 2,000,000 g/mol. The degree of branching DB of the polymers and dendrimers can be between 0 (linear polymer with no branching points) and 1 (fully branched dendrimer). Particular preference is given to polymers according to the invention having a molecular weight of 100,000 to 1,500,000 g/mol, very particularly preferably polymers having a molecular weight of 200,000 to 1,000,000 g/mol. The molecular weight is determined by GPC (=gel permeation chromatography) against an internal polystyrene standard.

In the embodiment according to the invention, the proportion of the structural elements of the formula (I) in the polymer is 0.01 to 100 mol %, preferably 1 to 95 mol %, particularly preferably 10 to 80 mol % and very particularly preferably 30 to 60 mol %.

Besides structural units of the formula (I), the compounds according to the invention preferably comprise further structural units M, which may optionally be substituted by $R^1$ and comply with the general definition indicated above.

M preferably represents, identically or differently, an aromatic or heteroaromatic ring system having 5 to 40 aromatic ring atoms, particularly preferably a benzene, naphthalene, anthracene, benzanthracene, fluorene, benzofluorene, dibenzofluorene, cis- or trans-indenofluorene, benzindenofluorene, dibenzindenofluorene, spirobifluorene, phenanthrene, benzophenanthrene or dihydrophenanthrene derivative, very particularly preferably a fluorene, spirobifluorene, cis-indenofluorene, trans-indenofluorene, phenanthrene or dihydrophenanthrene derivative.

$R_F$ preferably represents a partially fluorinated, non-aromatic substituent having 1 to 20 C atoms, particularly preferably having 1 to 12 C atoms, which may be saturated or unsaturated, linear, cyclic or branched and in which one or more adjacent or non-adjacent $CH_2$ groups may be replaced by O, S, $Si(R^2)_2$, $BR^2$, $NR^2$, $PR^2$, CO, C=S, C=$NR^2$, $PO(R^2)$, $PS(R^2)$, $R^2_{C=CR^2}$, C≡C, SO, $SO_2$, COO, O(CO)O or $CONR^2$.

The term "partially fluorinated" here and below is intended to be taken to mean that the substituent $R_F$, as defined above, has a substituent other than F at at least one free position of the carbon backbone.

$R_F$ very particularly preferably represents a partially fluorinated saturated linear, branched or cyclic alkyl group which contains 1 to 12 C atoms and in which one or more adjacent or non-adjacent $CH_2$ groups may optionally be replaced by O, S, $NR^2$, C=O, COO or $CONR^2$.

$R_F$ furthermore particularly preferably comprises one or more structural elements selected from the groups —$OCF_3$, —$SCF_3$, —$N(CF_3)_2$ and terminal aliphatic trifluoromethyl.

The compounds according to the invention, in particular if they are to be used for processing from solution, preferably contain linear or branched alkyl chains as substituents $R_F$ and $R^1$, particularly preferably those having a length of 1 to 12 C atoms.

The index b, the number of partially fluorinated radicals $R_F$ on a building block M, is preferably between one and five, very particularly preferably one or two.

It should explicitly be pointed out that two or more radicals $R_F$ and/or $R^1$ on one or more adjacent groups M may also form an aromatic or aliphatic ring system with one another. If a plurality of radicals $R_F$ and/or $R^1$ on an aromatic unit M form a ring system with one another, a Spiro compound may result. Spiro structures of this type represent preferred compounds according to the invention. Particular preference is given here to compounds derived from the fluorene or indenofluorene skeleton, very particularly preferably spirobifluorene derivatives.

Preferred structural units M-$(R_F)_b$ of the formula (I) are represented by the formulae (II) to (XXXIV) indicated below,

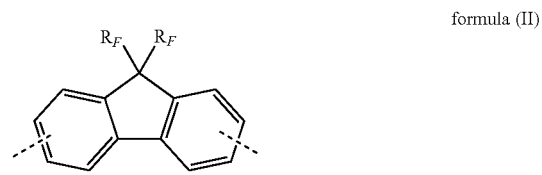

formula (II)

formula (III)

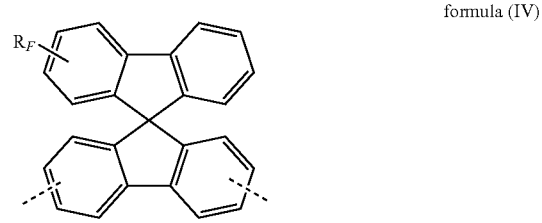

formula (IV)

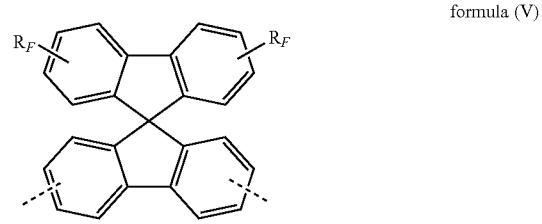

formula (V)

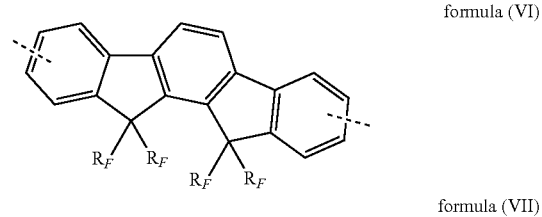

formula (VI)

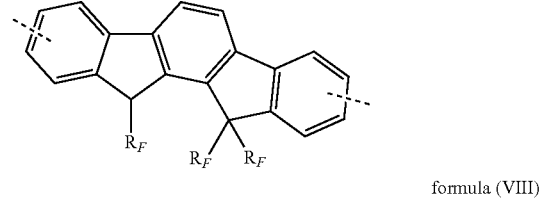

formula (VII)

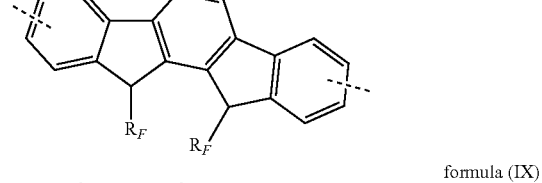

formula (VIII)

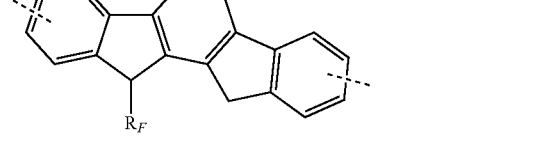

formula (IX)

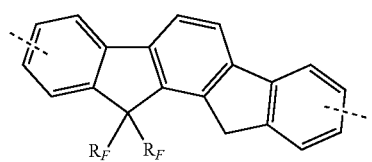
formula (X)
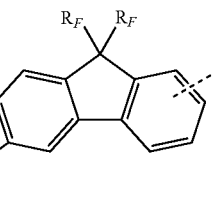
formula (XI)
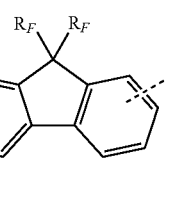
formula (XII)
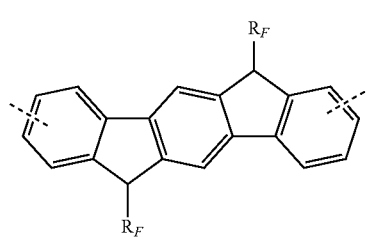
formula (XIII)
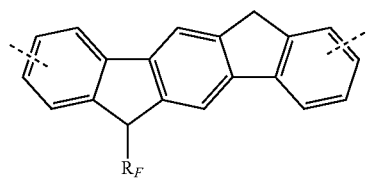
formula (XIV)
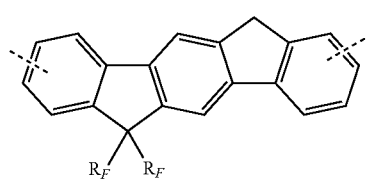
formula (XV)
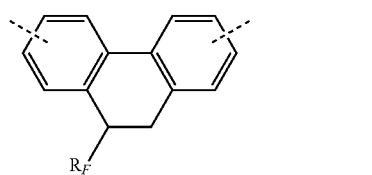
formula (XVI)
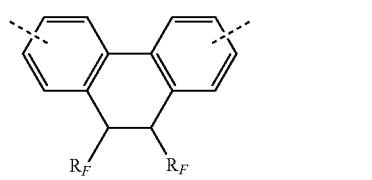
formula (XVII)
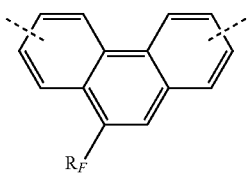
formula (XVIII)
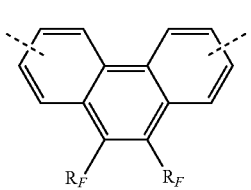
formula (XIX)
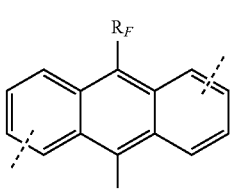
formula (XX)
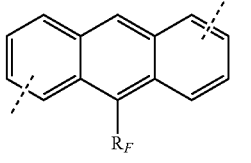
formula (XXI)
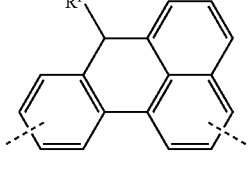
formula (XXII)
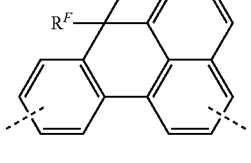
formula (XXIII)
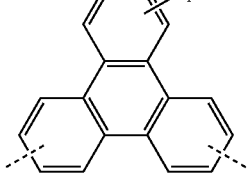
formula (XXIV)
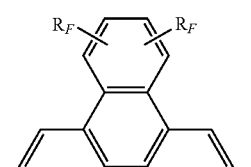
formula (XXV)

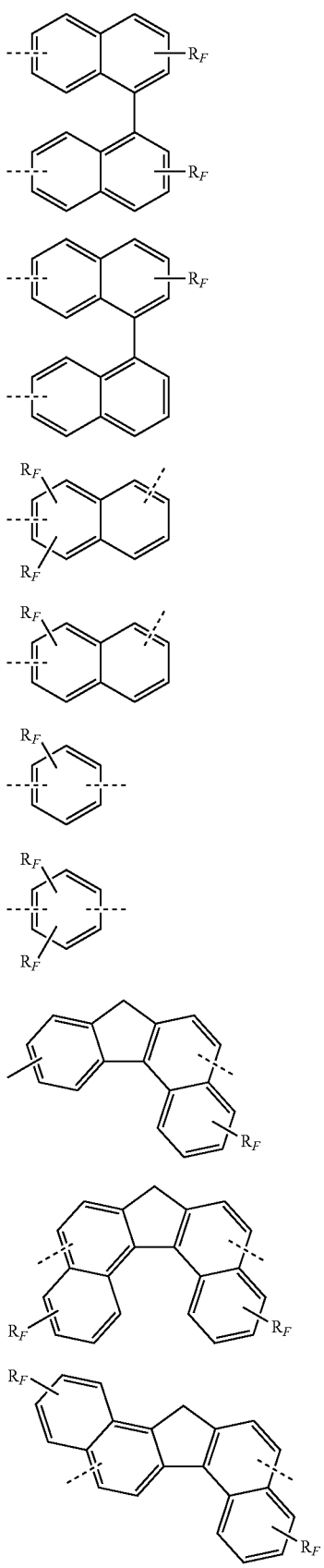

formula (XXVI)

formula (XXVII)

formula (XXVIII)

formula (XXIX)

formula (XXX)

formula (XXXI)

formula (XXXII)

formula (XXXIII)

formula (XXXIV)

where $R_F$ is as defined above, and the structural elements M may optionally be substituted at all H-substituted positions of the skeleton instead by one or more identical or different radicals $R^1$.

The dashed lines in the formulae (II) to (XXXIV) indicate potential linking points in the polymers according to the invention, without representing a limiting selection. In general, two such bonds are present per structural unit, but only one or more than two may also be present.

An aryl group in the sense of the present invention contains 6 to 40 C atoms; a heteroaryl group in the sense of the present invention contains 2 to 40 C atoms and at least one heteroatom, with the proviso that the sum of C atoms and heteroatoms is at least 5. The heteroatoms are preferably selected from N, O, S, P, Se, Si, Ge, Te, B and As. An aryl group or heteroaryl group here is taken to mean either a simple aromatic ring, i.e. benzene, or a simple heteroaromatic ring, for example pyridine, pyrimidine or thiophene, or a condensed aryl or heteroaryl group, for example naphthalene, anthracene, phenanthrene, quinoline, isoquinoline, benzothiophene, benzofuran or indole.

An aromatic or heteroaromatic ring system in the sense of the present invention is intended to be taken to mean a system which does not necessarily contain only aryl or heteroaryl groups, but instead in which, in addition, a plurality of aryl or heteroaryl groups may be interrupted by a short, non-aromatic unit, such as, for example, one or more C, N, S or O atoms. Thus, for example, systems such as 9,9'-spirobifluorene, 9,9-diaryl-fluorene, triarylamine or diaryl ether are also intended to be taken to be aromatic ring systems in the sense of the present invention. An aromatic or heteroaromatic ring system is likewise taken to mean systems in which a plurality of aryl or heteroaryl groups are linked to one another by single bonds, for example biphenyl, terphenyl or bipyridine.

An aromatic or heteroaromatic ring system, which may optionally be substituted, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, terphenylene, fluorene, spirobifluorene, benzofluorene, dibenzofluorene, dihydrophenanthrene, dihydropyrene, tetrahydropyrene, cis- or trans-indenofluorene, benzindenofluorene, dibenzindenofluorene, acenaphthene, truxene, isotruxene, spirotruxene, spiroisotruxene, furan, benzofuran, isobenzofuran, dibenzofuran, thio-phene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, 1,3,5-triazole, benzotriazole, 1,2,3-oxadiazole, 1,2,4-oxadiazole, 1,2,5-oxadia diazole, 1,2,3-thiadiazole, 1,2,4-thiadiazole, 1,2,5-thiadiazole, 1,3,4-thia-diazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For the purposes of the present invention, an aliphatic compound, in which, in addition, individual H atoms or CH₂ groups may be substituted by the groups mentioned above, is particularly preferably taken to mean the radicals methyl, ethyl, n-propyl, i-propyl, cyclopropyl, n-butyl, i-butyl, s-butyl, t-butyl, cyclobutyl, 2-methylbutyl, n-pentyl, s-pentyl, cyc neopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, cyclooctadienyl, ethynyl, propynyl, butynyl, pentynyl, hexynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methyl-butoxy.

Examples of preferred building blocks $M-(R_F)_b$ of the formula (I), without wishing to represent a limiting selection, are:

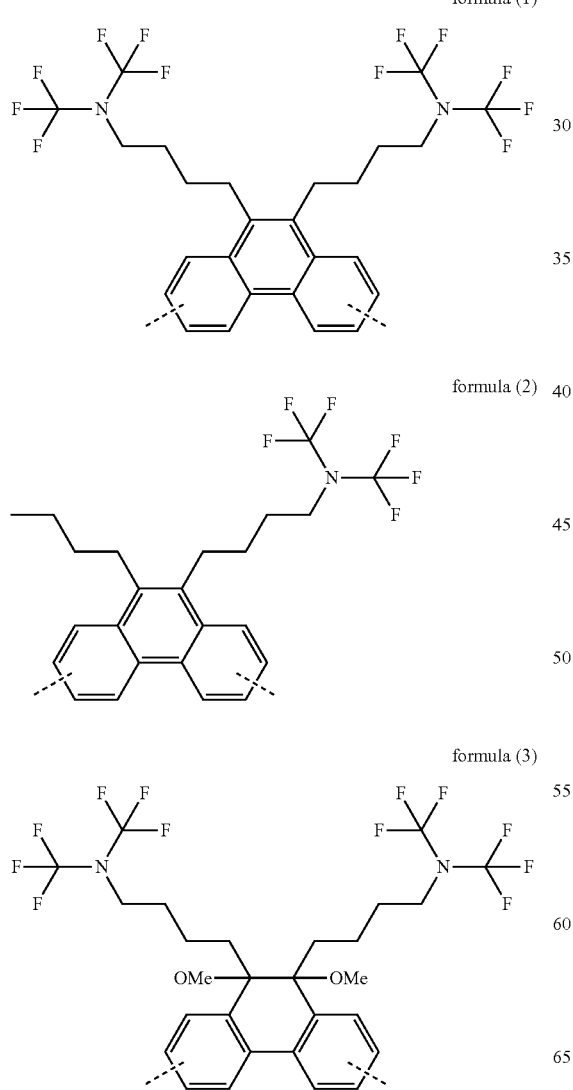

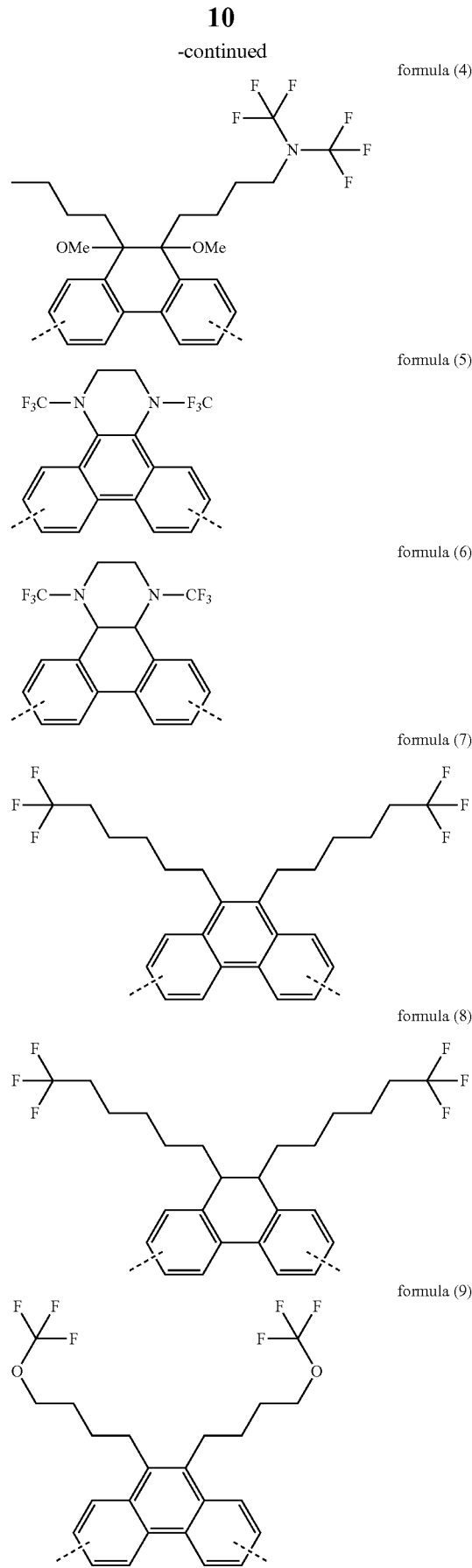

formula (10)
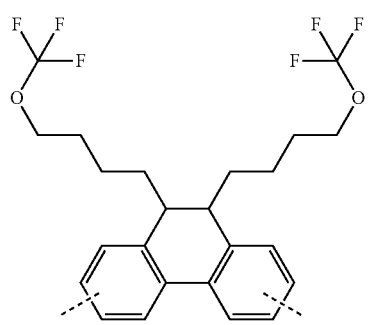
formula (11)
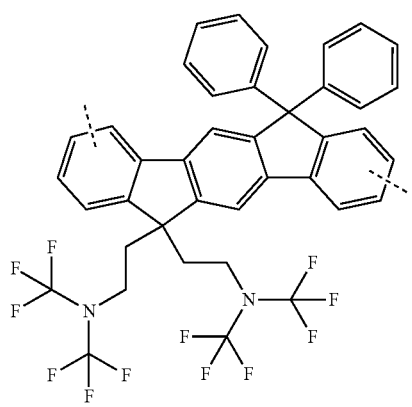
formula (12)
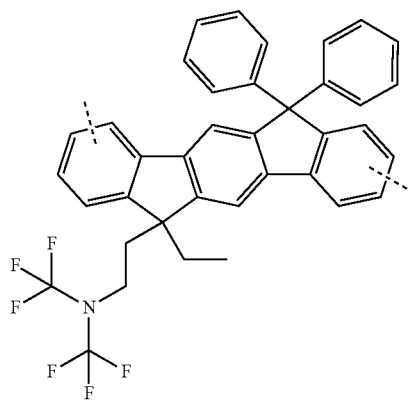
formula (13)
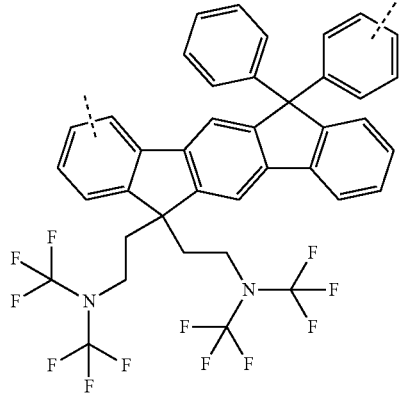
formula (14)
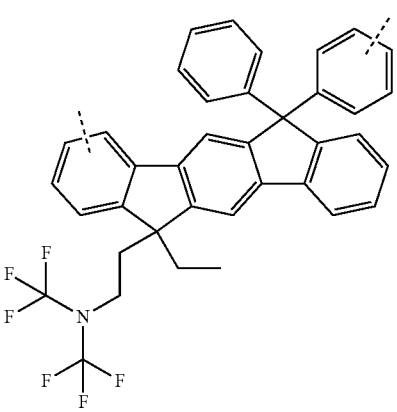
formula (15)
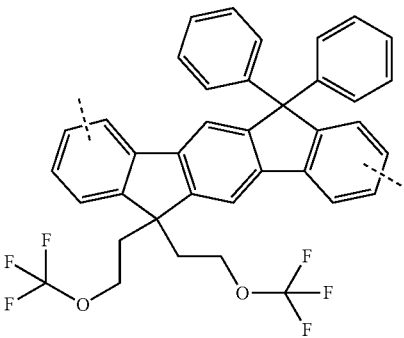
formula (16)
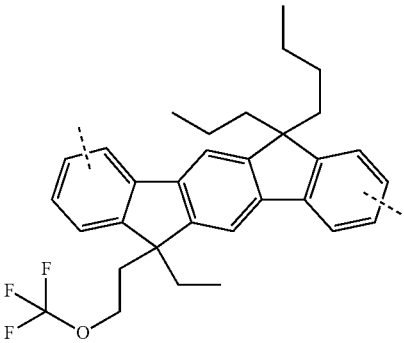
formula (17)
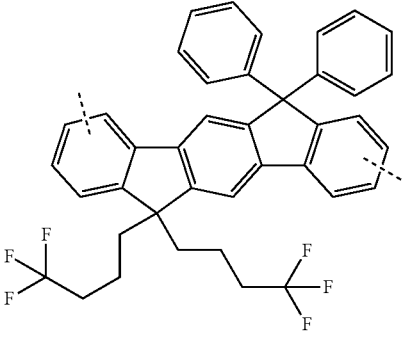

formula (18)
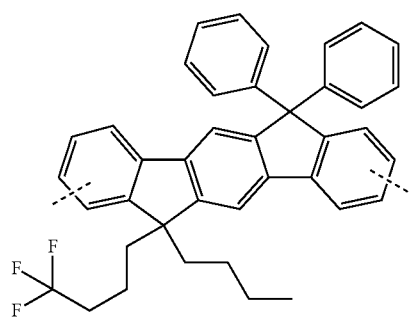
formula (19)
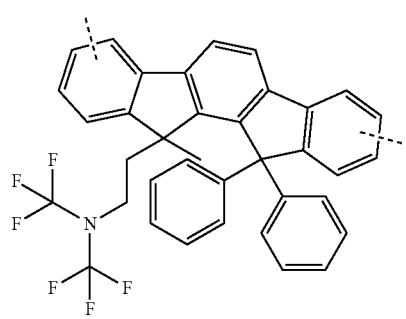
formula (20)
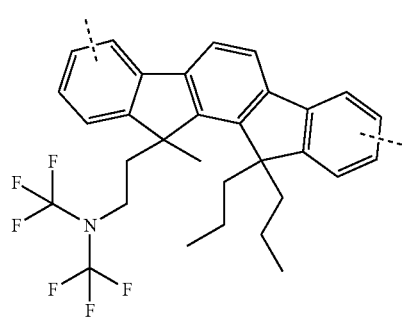
formula (21)
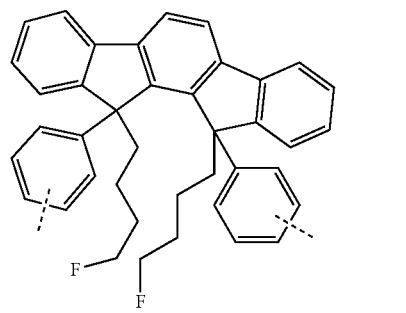
formula (22)
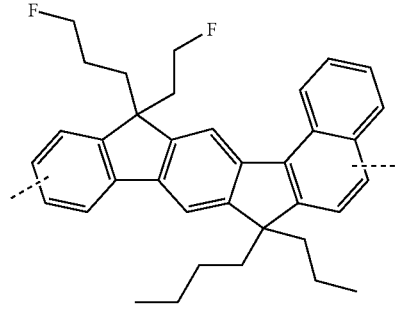
formula (23)
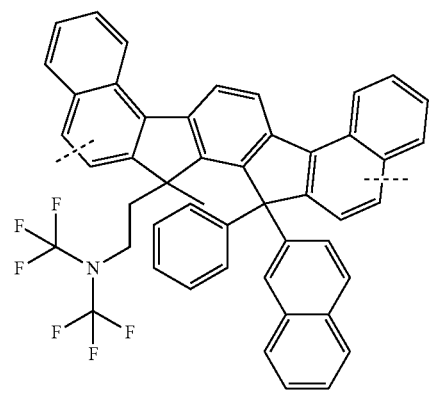
formula (24)
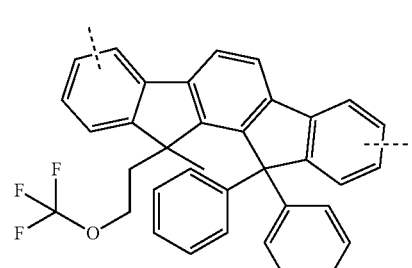
formula (25)
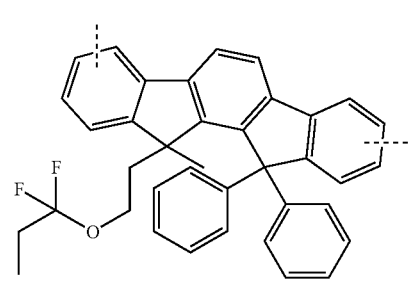
formula (26)
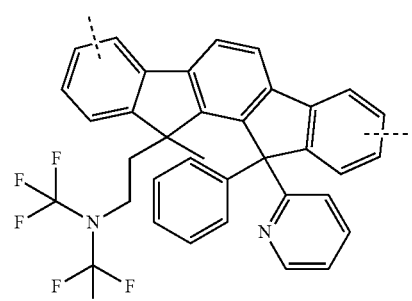
formula (27)
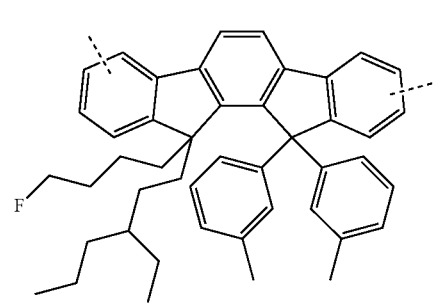

formula (28)
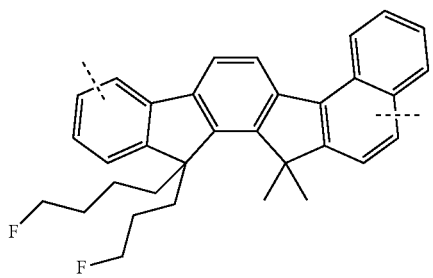
formula (29)
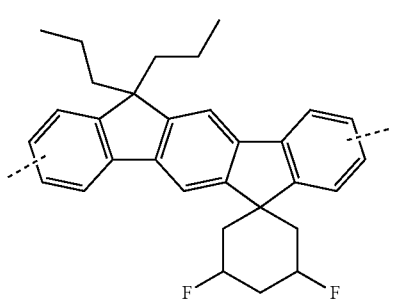
formula (30)
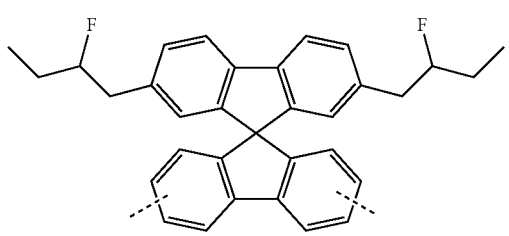
formula (31)
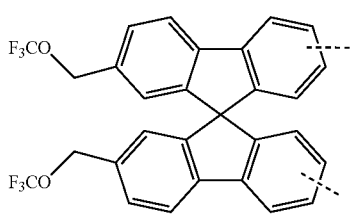
formula (32)
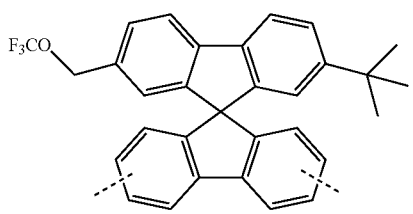
formula (33)
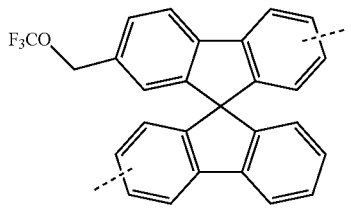
formula (34)
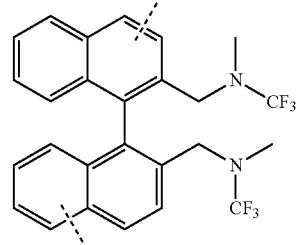
formula (35)
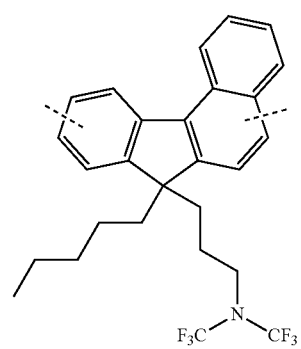
formula (36)
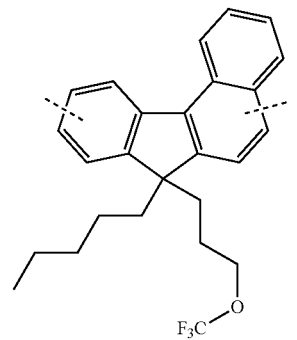
formula (37)
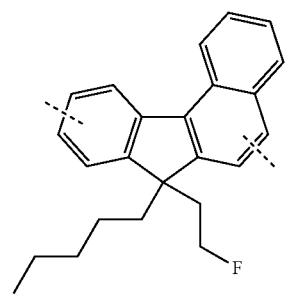
formula (38)
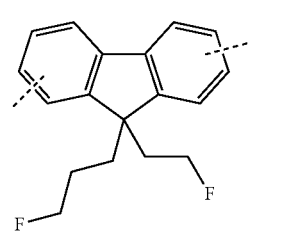

formula (39)
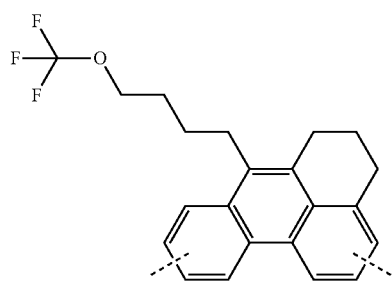
formula (40)
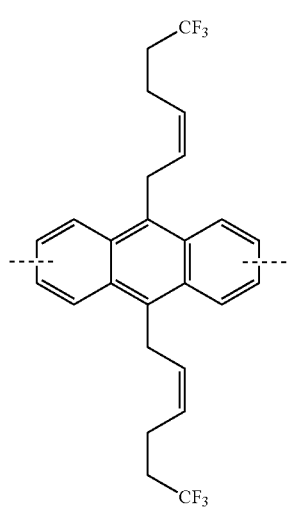
formula (41)
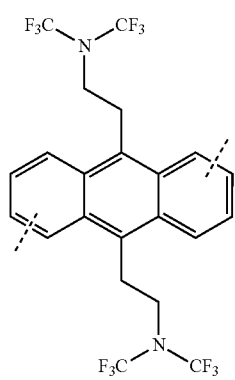
formula (42)
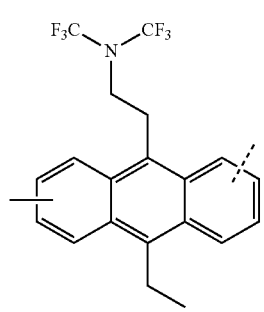
formula (43)
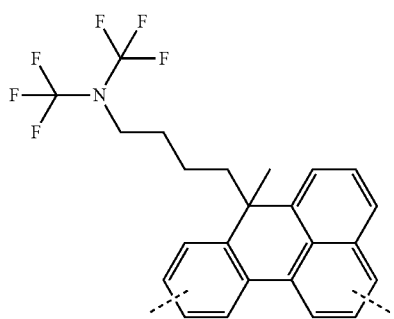
formula (44)
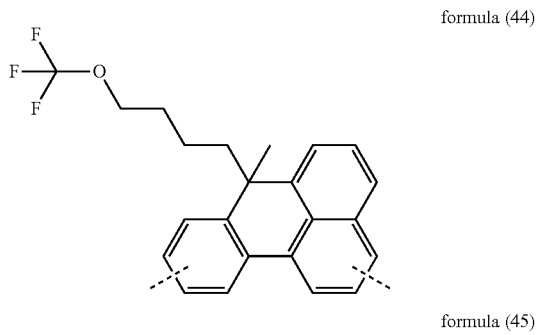
formula (45)
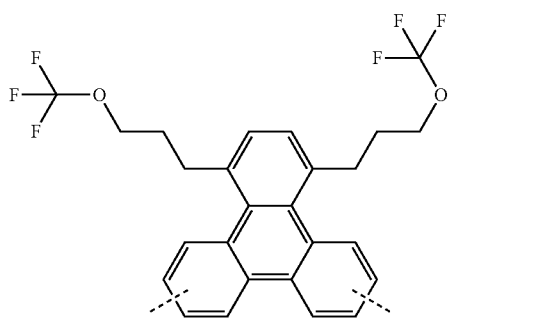
formula (46)
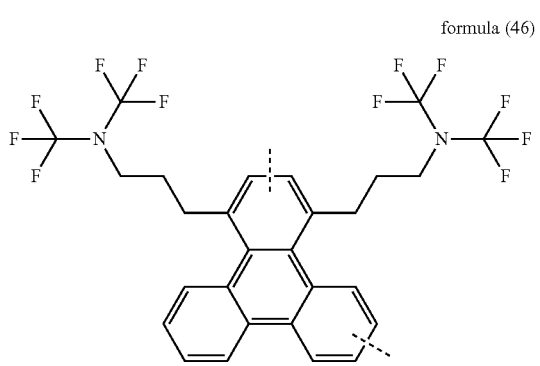
formula (47)
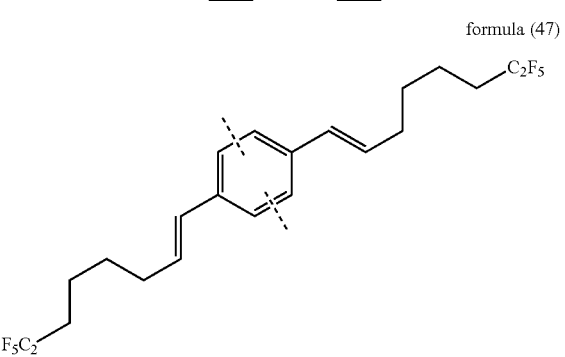

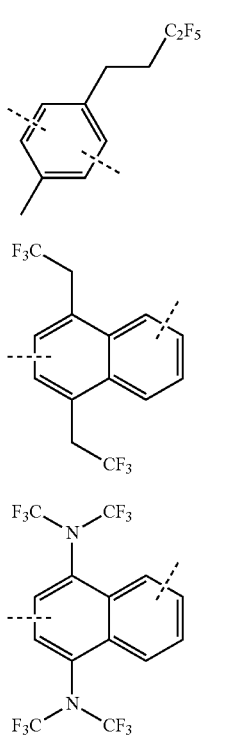

formula (48)

formula (49)

formula (50)

where the compounds may optionally be substituted at all free positions or positions that are substituted by H by identical or different radicals R¹.

The dashed lines in the formulae (1) to (50) indicate potential linking points in the polymers according to the invention, without representing a limiting selection. In general, two such bonds are present per structural unit, but only one or more than two may also be present.

The compounds according to the invention preferably contain, as groups M, a plurality of different structural units. These are, inter alia, those as disclosed and listed extensively in WO 02/077060 A1 and in WO 2005/014689 A2. The technical teaching of the above-mentioned applications which is relevant in this respect is hereby incorporated into the present application by way of reference.

The further structural units can be assigned, for example, to the following groups:
group 1: units which influence the hole-injection and/or hole-transport properties of the polymers;
group 2: units which influence the electron-injection and/or electron-transport properties of the polymers;
group 3: units which have combinations of individual units from group 1 and group 2;
group 4: units which modify the emission characteristics to such an extent that electrophosphorescence can be obtained instead of electrofluorescence;
group 5: units which improve transfer from the singlet state to the triplet state;
group 6: units which influence the emission colour of the resultant polymers;
group 7: units which are typically used as polymer backbone;
group 8: units which influence the film morphology and/or rheology of the resultant polymers.

Structural units from group 1 which have hole-injection and/or hole-transport properties are, for example, triarylamine, benzidine, tetraaryl-paraphenylenediamine, triarylphosphine, phenothiazine, phenoxazine, dihydrophenazine, thianthrene, dibenzo-para-dioxin, phenoxathiyne, carbazole, azulene, thiophene, pyrrole and furan derivatives and further O—, S— or N— containing heterocycles having a high HOMO (HOMO=highest occupied molecular orbital). These arylamines and heterocycles preferably result in an HOMO in the polymer of greater than −5.8 eV (against vacuum level), particularly preferably greater than −5.5 eV.

Structural units from group 2 which have electron-injection and/or electron-transport properties are, for example, pyridine, pyrimidine, pyridazine, pyrazine, oxadiazole, quinoline, quinoxaline, anthracene, benzanthracene, pyrene, perylene, benzimidazole, triazine, ketone, phosphine oxide and phenazine derivatives, but also triarylboranes and further O—, S— or N-containing heterocycles having a low LUMO (LUMO=lowest unoccupied molecular orbital). These units in the polymer preferably result in an LUMO of less than −1.5 eV (against vacuum level), particularly preferably less than −2.0 eV.

It may be preferred for the polymers according to the invention to comprise units from group 3 in which structures which increase the hole mobility and structures which increase the electron mobility (i.e. units from groups 1 and 2) are bonded directly to one another or structures which increase both the hole mobility and the electron mobility. Some of these units can serve as emitters and shift the emission colour into the green, yellow or red. Their use is thus suitable, for example, for the generation of other emission colours from originally blue-emitting polymers.

Structural units from group 4, so-called triplet emitter units, are those which are able to emit light from the triplet state with high efficiency, even at room temperature, i.e. exhibit electrophosphorescence instead of electro-fluorescence, which frequently causes an increase in the energy efficiency. A triplet emitter unit in the sense of the present invention is taken to mean a compound which comprises a triplet emitter. Triplet emitter in the sense of the present invention is taken to mean all compounds which are capable of emitting light in the visible or NIR region by transfer from a triplet state into an energetically lower state. The term phosphorescence is also used here. Suitable for this purpose are firstly compounds which contain heavy atoms having an atomic number of greater than 36. Preference is given to compounds which contain d- or f-transition metals which satisfy the above-mentioned condition. Particular preference is given here to corresponding structural units which contain elements from groups 8 to 10 of the Periodic Table (Ru, Os, Rh, Ir, Pd, Pt). Suitable structural units for the polymers according to the invention here are, for example, various complexes, as described, for example, in WO 02/068435 A1, WO 02/081488 A1 and EP 1239526 A2. Corresponding monomers are described in WO 02/068435 A1 and in WO 2005/042548 A1. It is preferred in accordance with the invention to employ triplet emitters which emit in the visible spectral region (red, green or blue). The triplet emitter may be part of the back-bone of the polymer (i.e. in the main chain of the polymer) or it may be located in a side chain of the polymer.

Structural units from group 5 are those which improve transfer from the singlet state to the triplet state and which, employed in support of the above-mentioned triplet emitter units, improve the phosphorescence properties of these structural elements. Suitable for this purpose are, in particular, carbazole and bridged carbazole dimer units, as described, for example, in WO 2004/070772 A2 and WO 2004/113468 A1. Also suitable for this purpose are ketones, phosphine oxides, sulfoxides, sulfones, silane derivatives and similar compounds, as described, for example, in WO 2005/040302 A1.

Structural units from group 6, besides those mentioned above, are those which have at least one further aromatic structure or another conjugated structure which does not fall under the above-mentioned groups, i.e. which have only little influence on the charge-carrier mobilities, are not organometallic complexes or do not influence singlet-triplet transfer. Structural elements of this type can influence the emission colour of the resultant polymers. Depending on the unit, they can therefore also be employed as emitters. Preference is given here to aromatic structures having 6 to 40 C atoms and also tolan, stilbene or bisstyrylarylene derivatives, each of which may be substituted by one or more radicals $R^1$. Particular preference is given here to the incorporation of 1,4-phenylene, 1,4-naphthylene, 1,4- or 9,10-anthrylene, 1,6-, 2,7- or 4,9-pyrenylene, 3,9- or 3,10-perylenylene, 4,4'-biphenylylene, 4,4''-terphenylylene, 4,4'-bi-1,1'-naphthylylene, 4,4'-tolanylene, 4,4'-stilbenylene, 4,4''-bisstyrylarylene, benzothiadiazole and corresponding oxygen derivatives, quinoxaline, phenothiazine, phenoxazine, dihydrophenazine, bis(thiophenyl)arylene, oligo(thiophenylene), phenazine, rubrene, pentacene or perylene derivatives, which are preferably substituted, or preferably conjugated push-pull systems (systems which are substituted by donor and acceptor substituents) or systems such as squarines or quinacridones, which are preferably substituted.

Structural units from group 7 are units which contain aromatic structures having 6 to 40 C atoms, which are typically used as polymer backbone. These are, for example, 4,5-dihydropyrene derivatives, 4,5,9,10-tetrahydropyrene derivatives, fluorene derivatives, 9,9'-spirobifluorene derivatives, phenanthrene derivatives, 9,10-dihydrophenanthrene derivatives, 5,7-dihydrodibenzoxepine derivatives and cis- and trans-indenofluorene derivatives, but basically also all similar structures which would, after polymerisation, result in a conjugated, bridged or unbridged polyphenylene or polyphenylene-vinylene homopolymer. Here too, the said aromatic structure may contain heteroatoms, such as O, S or N, in the backbone or a side chain.

Structural units from group 8 are those which influence the film morphology and/or rheology of the polymers, such as, for example, siloxanes, long alkyl chains or fluorinated groups, but also particularly rigid or flexible units, such as, for example, liquid crystal-forming units or crosslinkable groups.

Preferred polymers according to the invention are those in which at least one structural unit has charge-transport properties, i.e. polymers which comprise, inter alia, at least one unit selected from groups 1 and 2.

Preferred compounds according to the invention are polymers which, besides structural units of the formula (I), at the same time additionally comprise one or more units selected from groups 1 to 8. It may furthermore be preferred for more than one structural unit from one group to be present at the same time.

It is likewise preferred for the polymers according to the invention to comprise units which improve charge transport and/or charge injection, i.e. units from group 1 and/or 2; a proportion of 0.5 to 50 mol % of these units is particularly preferred; a proportion of 1 to 10 mol % of these units is very particularly preferred.

It is furthermore particularly preferred for the polymers according to the invention to comprise structural units from group 7 and units from group 1 and/or 2. It is particularly preferred for the sum of structural units of the formula (I), of units from group 7 and units from group 1 and/or 2 of the polymer to be at least 50 mol %, based on all units of the polymer, where 0.5 to 30 mol % are preferably units from group 1 and/or 2.

The way in which the above-mentioned copolymers having block-like structures can be obtained and which further structural elements are particularly preferred for this purpose is described in detail, for example, in WO 2005/014688 A2. This is incorporated into the disclosure content of the present application by way of reference. It should likewise be emphasised at this point that the polymer may also have dendritic structures.

The synthesis of the above-described units from groups 1 to 8 and of the further emitting units is known to the person skilled in the art and is described in the literature, for example in WO 2005/014689 A2, WO 2005/030827 A1 and WO 2005/030828 A1 . These documents and the literature cited therein are incorporated by way of reference into the technical teaching disclosed in this application.

The compounds according to the invention are generally synthesised by a polymerisation reaction with one or more different monomer building blocks, where at least one monomer incorporated into the polymer results in structural units of the formula (I). Suitable polymerisation reactions are known to the person skilled in the art and are described in the literature. Particularly suitable and preferred polymerisation reactions which result in C—C or C—N links are the following: SUZUKI, YAMAMOTO, STILLE, HECK, NEGISHI, SONOGASHIRA, HIYAMA or HARTWIG-BUCHWALD polymerisation. The way in which the polymerisation can be carried out by these methods and the way in which the polymers can then be separated off from the reaction medium and purified is known to the person skilled in the art and is described in detail in the literature, for example in WO 03/048225 A2, WO 2004/037887 A2 and WO 2004/037887 A2.

The present invention thus also relates to a process for the preparation of the polymers according to the invention, which is characterised in that they are prepared by SUZUKI, YAMAMOTO, STILLE, HECK, NEGISHI, SONOGASHIRA, HIYAMA, ULLMANN, WITTIG or HARTWIG-BUCHWALD polymerisation.

The dendrimers according to the invention can be prepared by processes known to the person skilled in the art or analogously thereto. Suitable processes are described in the literature, for example in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6, WO 02/067343 A1 and WO 2005/026144 A1.

For the synthesis of the polymers according to the invention, the corresponding monomers of the formula (XXXV) are required.

formula (XXXV)

Monomers which result in structural units of the formula (I) in the polymers according to the invention are compounds which are correspondingly substituted and have at either one, two or three, preferably two, positions suitable functionalities which allow this monomer unit to be incorporated into the polymer. The present invention thus likewise relates to these monomers which have structures of the formula (XXXV). The symbols and indices M, $R_F$ and b used in formula (XXXV) are defined as already described above. The group X represents, identically or differently, a leaving group which is suitable for a polymerisation reaction, enabling incorporation of the monomer building blocks into polymeric compounds. X preferably represents a chemical functionality which is selected, identically or differently, from the class of the halogens, O-tosylates, O-triflates, O-sulfonates, boric acid esters, partially fluorinated silyl groups, diazonium groups and organotin compounds. The index n can adopt the values 1, 2 or 3, preferably 2.

The skeleton of the monomer compounds can be functionalised by standard methods, for example by Friedel-Crafts alkylation or acylation. Furthermore, the skeleton can be halogenated by standard methods of organic chemistry. The halogenated compounds can optionally be reacted further in additional functionalisation steps. For example, the halogenated compounds can be employed as starting materials for conversion into polymers, oligomers or dendrimers, either directly or after conversion into a boronic acid derivative or organotin derivative.

The said methods merely represent a selection from the reactions known to the person skilled in the art which can be employed by him, without being inventive, for the synthesis of the compounds according to the invention.

It may be preferred to use the polymers according to the invention not as the pure substance, but instead as a mixture (blend) together with further polymeric, oligomeric, dendritic or low-molecular-weight substances of any desired type. These may, for example, improve the electronic properties or themselves emit. A mixture above and below is taken to mean a composition which comprises at least one polymeric component.

The present invention thus furthermore relates to a mixture (blend) which comprises one or more polymers according to the invention and one or more further polymeric, oligomeric, dendritic or low-molecular-weight substances.

In a further embodiment of the present invention, it is preferred for a mixture to comprise a polymer according to the invention comprising structural units of the formula (I) and a low-molecular-weight substance.

In a further embodiment according to the invention, it is preferred for a mixture to comprise a polymer according to the invention, an emitter, which is either present in the polymer according to the invention or, as in the above-mentioned embodiments, is admixed as low-molecular-weight substance, and further low-molecular-weight substances. These low-molecular-weight substances can have the same functionalities as mentioned for possible monomer building blocks in groups 1 to 8.

The present invention furthermore relates to formulations comprising one or more polymers according to the invention and at least one solvent. The way in which solutions of this type can be prepared is known to the person skilled in the art and is described, for example, in WO 02/072714 A1, WO 03/019694 A2 and the literature cited therein.

Suitable and preferred solvents are, for example, toluene, anisoles, xylenes, methyl benzoate, dimethylanisoles, mesitylenes, tetralin, veratrols and tetrahydrofuran, or mixtures of the above-mentioned substances.

These solutions can be used in order to produce thin polymer layers, for example by area-coating methods (for example spin coating) or by printing methods (for example ink-jet printing).

The compounds according to the invention preferably have a glass-transition temperature TG of greater than 70° C., particularly preferably greater than 100° C. and very particularly preferably greater than 130° C.

The polymers, mixtures and formulations according to the invention can be used in electronic or electro-optical devices or for the production thereof. Furthermore, the compounds according to the invention can be used as surface-active substances, for example as surfactants.

The present invention relates to the use of the polymers, mixtures and formulations according to the invention in electronic or electro-optical devices, preferably in organic electroluminescent devices (OLEDs), organic field-effect transistors (OFETs), organic integrated circuits (O-ICs), organic thin-film transistors (O-TFTs), organic solar cells (O-SCs), laser diodes (O-lasers), organic photovoltaic elements or devices (OPVs) or organic photoreceptors (OPCs), particularly preferably in organic electroluminescent devices (OLEDs).

The present application focuses on the use of the compounds according to the invention in organic electroluminescent devices, especially OLEDs. However, it is possible for the person skilled in the art, without further inventive step, also to employ the compounds according to the invention for further uses in other electronic devices.

For the purposes of the present invention, it is preferred for the polymer, oligomer or dendrimer according to the invention to be present as a layer (or in a layer) in the electronic device.

The present invention thus also relates to a layer, in particular an organic layer, comprising one or more polymers according to the invention.

The compounds are preferably used in organic electronic devices comprising at least one layer comprising one or more of the polymers according to the invention. Preference is given to the use, in particular, in organic electroluminescent devices comprising an anode, a cathode and at least one emitting layer, characterised in that at least one layer comprises at least one polymer according to the invention comprising structural elements of the formula (I).

In a further embodiment, it is preferred for the polymer comprising structural elements of the formula (I) to be employed in an emitting layer together with an emitting compound. The mixture of the polymer comprising structural elements of the formula (I) and the emitting compound then comprises between 99 and 1% by weight, preferably between 98 and 60% by weight, particularly preferably between 97 and 70% by weight, in particular between 95 and 75% by weight, of the polymer, based on the entire mixture comprising emitter and matrix material. Correspondingly, the mixture comprises between 1 and 99% by weight, preferably between 2 and 40% by weight, particularly preferably between 3 and 30% by weight, in particular between 5 and 25% by weight, of the emitter, based on the entire mixture comprising emitter and matrix material.

In still a further embodiment of the invention, the compounds according to the invention are employed as hole-transport material or as hole-injection material. The compound is preferably employed in a hole-transport or hole-injection layer. These hole-injection layers according to the invention are, for example, triarylamines, carbazoles, silanes or phosphines.

A hole-injection layer in the sense of the present invention is a layer which is directly adjacent to the anode. A hole-transport layer in the sense of the present invention is a layer which is located between a hole-injection layer and an emission layer. If compounds according to the invention are used as hole-transport or hole-injection material, it may be preferred for them to be doped with electron-acceptor compounds, for example with $F_4$-tetra-cyanoquinodimethane (TCNQ) or with compounds as described in EP 1476881 or EP 1596445.

In addition, the polymers according to the invention can be used in charge-blocking layers. These charge-blocking layers may consist of various suitable materials, including aluminium oxide, polyvinylbutyral, silane and mixtures thereof. This layer, which is generally applied by known coating techniques, can have any effective thickness, for example 0.05 to 0.5 µm.

In still a further embodiment of the present invention, the compounds according to the invention are employed as electron-transport material. It is preferred here for one or more substituents $R_F$ and/or $R^1$ to comprise at least one unit C=O, P(=O), SO and/or $SO_2$. These groups are particularly preferably bonded directly to the central unit according to the invention and furthermore particularly preferably contain a further one or, in the case of phosphine oxide, two further aromatic substituents. Electron conductors according to the invention can be, for example, benzimidazoles, triazines, nitriles, nitro compounds or boranes.

The present invention furthermore relates to electronic or opto-electronic components, preferably organic electroluminescent devices (OLEDs), organic field-effect transistors (OFETs), organic integrated circuits (O-ICs), organic thin-film transistors (TFTs), organic solar cells (O-SCs), organic laser diodes (O-lasers), organic photovoltaic elements or devices (OPVs) or organic photoreceptors (OPCs), particularly preferably organic electro-luminescent devices having one or more active layers, where at least one of these active layers comprises one or more polymers according to the invention. The active layer can be, for example, a light-emitting layer, a charge-transport layer and/or a charge-injection layer.

The way in which OLEDs can be produced is known to the person skilled in the art and is described, for example, in detail as a general process in WO 2004/070772 A2, which should be adapted correspondingly for the individual case.

An organic electroluminescent device is preferably characterised in that one or more layers are produced from solution, such as, for example, by spin coating, or by means of any desired printing process, such as, for example, roll to roll, screen printing, flexographic printing or offset printing, but particularly preferably LITI (light induced thermal imaging, thermal transfer printing), ink-jet printing, dipping processes or spray processes. Soluble compounds are necessary for this purpose. Surprisingly, high solubility can be achieved here by the substitutions according to the invention.

Apart from the cathode, anode and emitting layer, the organic electroluminescent device may also comprise further layers. These can be selected, for example, from charge carrier injection, charge carrier transport and charge carrier blocking layers (T. Matsumoto et al., *Multiphoton Organic EL Device Having Charge Generation Layer*, IDMC 2003, Taiwan; Session 21 OLED (5)). However, it should be pointed out that each of these layers does not necessarily have to be present and a plurality of layers having the same function may also be present.

In a further preferred embodiment of the present invention, the organic electroluminescent device comprises a plurality of emitting layers, where at least one layer comprises at least one compound according to the invention. The emission layers preferably have a plurality of emission maxima between 380 nm and 750 nm, resulting overall in white emission in this case. Particular preference is given to three-layer systems, where at least one of these layers comprises at least one polymer according to the invention and where the three layers exhibit blue, green and orange or red emission (for the basic structure see, for example, WO 05/011013).

The present invention thus relates both to the devices themselves and also to the use of the compounds according to the invention in the corresponding devices.

All preferred and not explicitly preferred features of the above-mentioned polymers according to the invention, their use in electronic devices and the electronic devices themselves can be combined with one another as desired. All resultant combinations are likewise part of the present invention.

The compounds according to the invention have one or more of the following advantageous properties, preferably on use in organic electroluminescent devices:

1. The compounds according to the invention have a low LUMO (lowest unoccupied molecular orbital) and are consequently easier to reduce. This results in easier electron injection and thus a lower operating voltage.
2. The compounds according to the invention have good differentiability with respect to solubility and wetting properties in order to be able to achieve multilayered systems. This is based on adhesive fluorine-fluorine interactions between the partially fluorinated side chains of the compounds according to the invention.
3. The compounds according to the invention increase the lifetime and efficiency, in particular of blue-emitting organic electroluminescent devices for high-quality applications.

The following examples are intended to explain the present invention in greater detail without restricting it. In particular, the features, properties and advantages described therein of the defined compounds on which the relevant example is based can also be applied to other compounds which are not mentioned in detail, but fall within the scope of protection of the claims, unless stated otherwise elsewhere.

WORKING EXAMPLES

Preparation of the Polymers

The monomeric compounds for the synthesis of the polymers according to the invention can be prepared by methods described in the prior art, where the person skilled in the art will be able to apply the methods to the specific case in question without being inventive. Processes for the synthesis of indenofluorene derivatives which are substituted by alkyl groups in the 9-positions are disclosed, for example, in WO 04/113412.

Processes for the synthesis of the partially fluorinated side chains according to the invention, especially those containing —$OCF_3$, —$SCF_3$ and —$N(CF_3)_2$ groups, are disclosed in detail in WO 06/072401 and WO 08/003447.

Preparation of the Polymers

Polymers P1 to P6 according to the invention are synthesised using the following monomers (per cent data=mol %)

by SUZUKI coupling in accordance with the general procedure from WO 03/048225 A2.
EXAMPLE 1
Polymer P1
EXAMPLE 2
Polymer P2
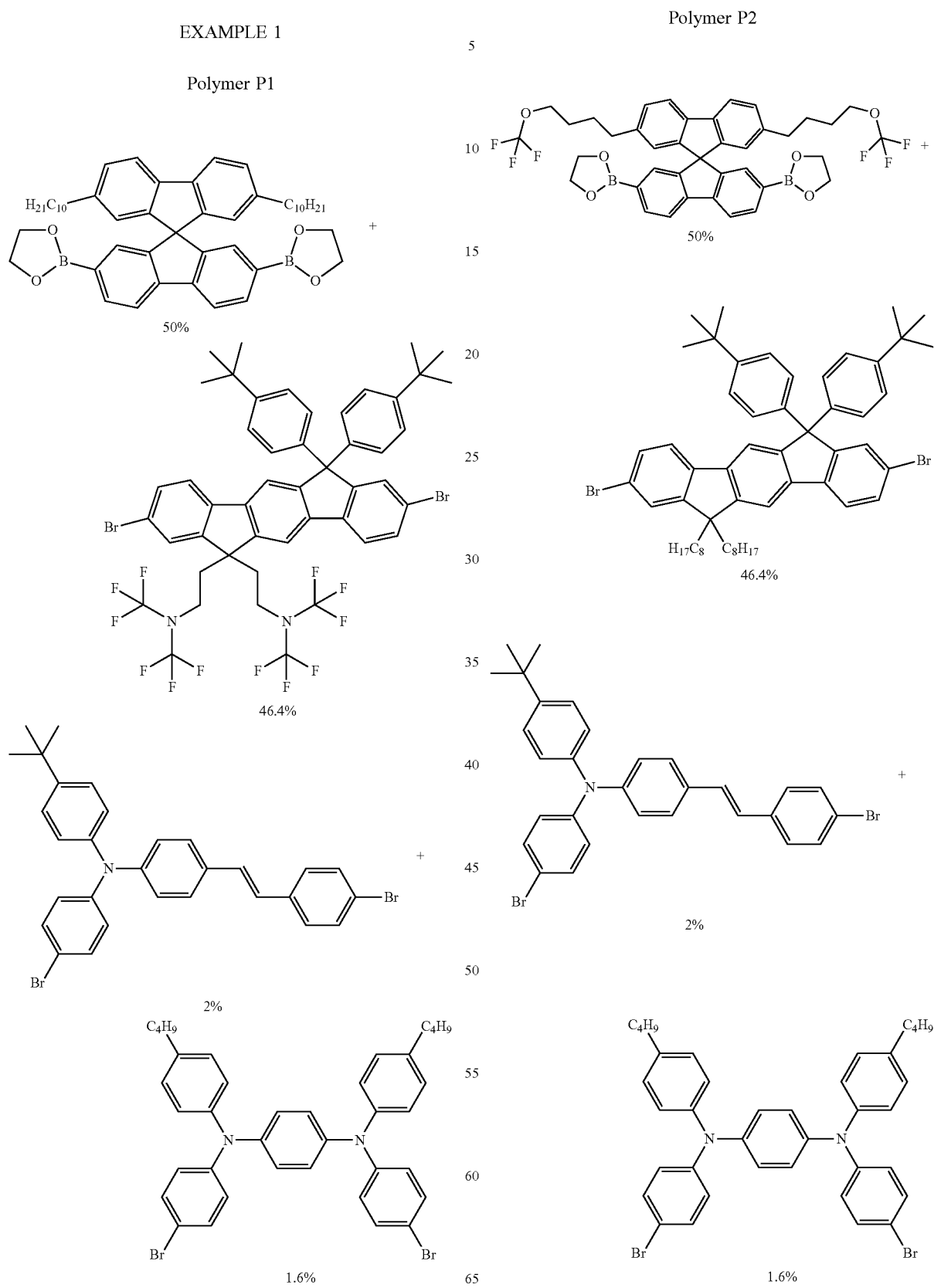

EXAMPLE 3
Polymer P3
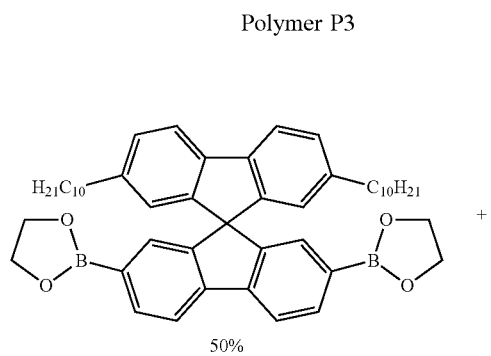
50%
EXAMPLE 4
Polymer P4
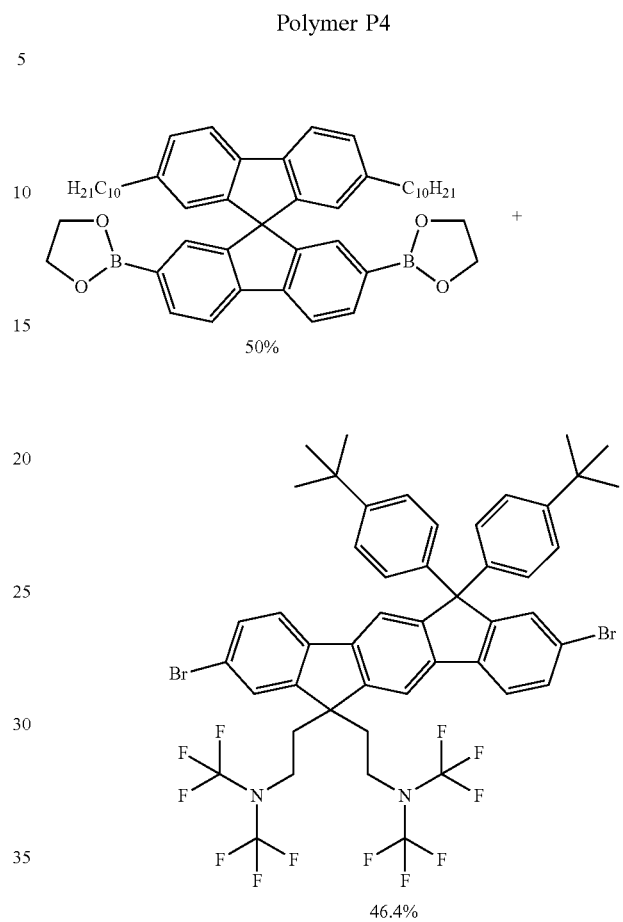
50%
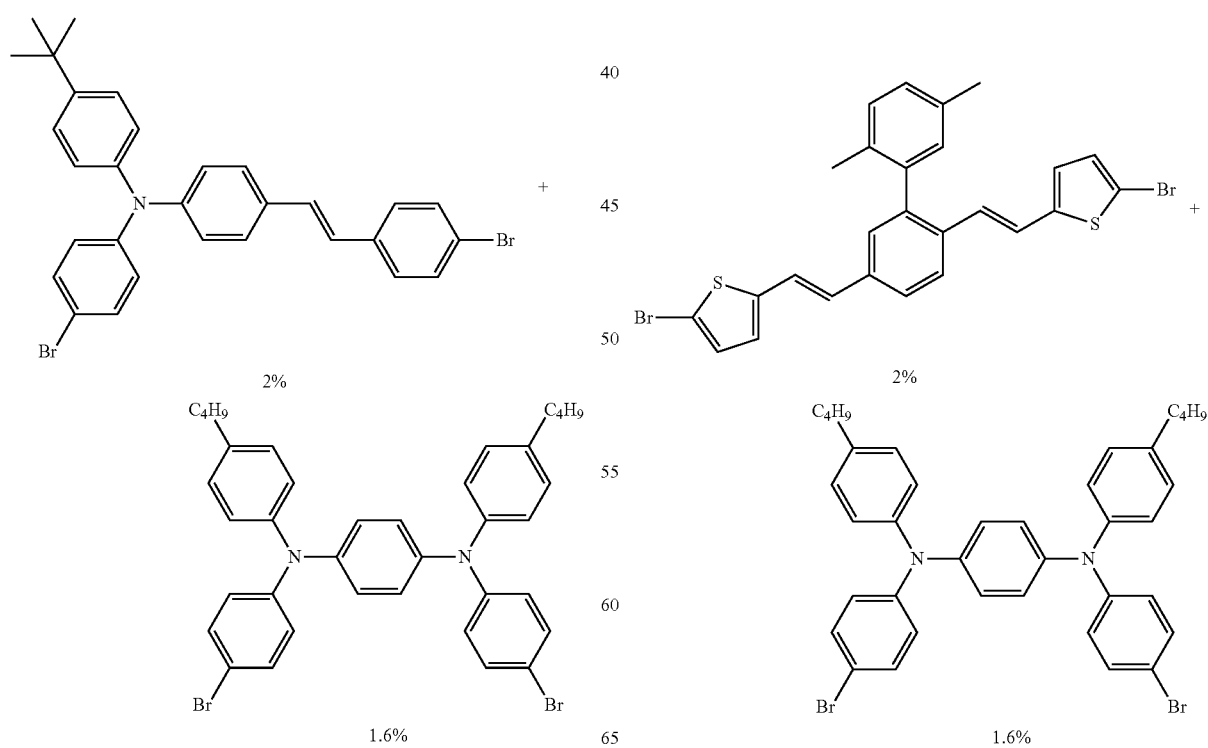

EXAMPLE 5
Polymer P5
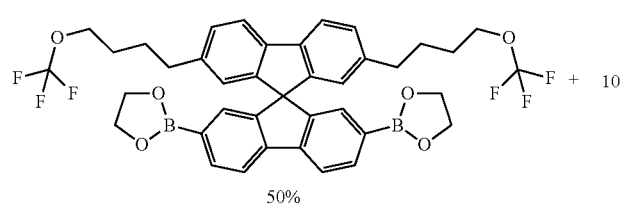
50%
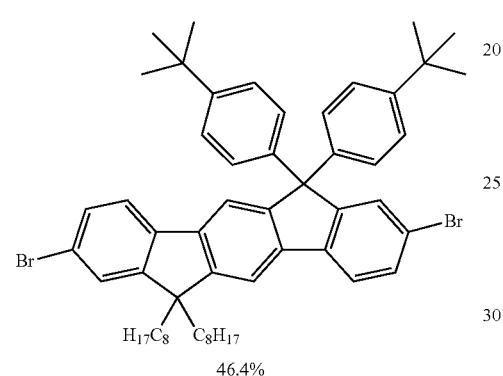
46.4%
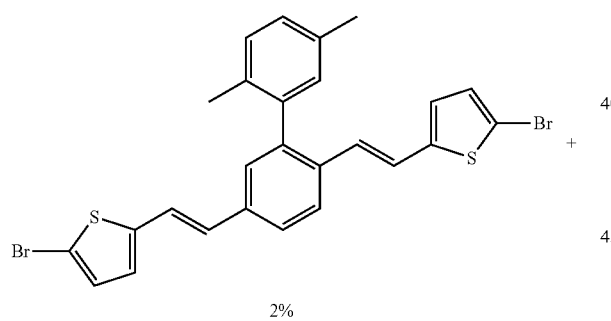
2%
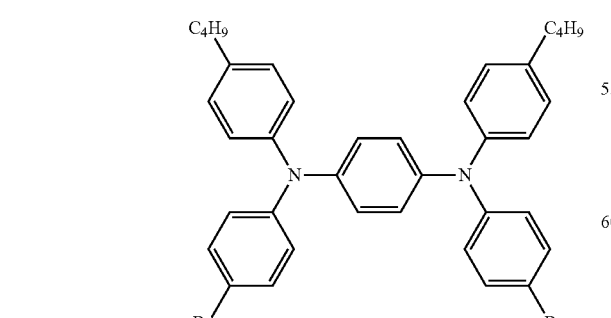
1.6%
EXAMPLE 6
Polymer P6
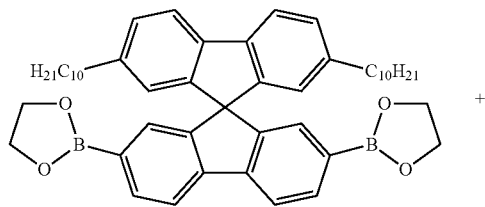
50%
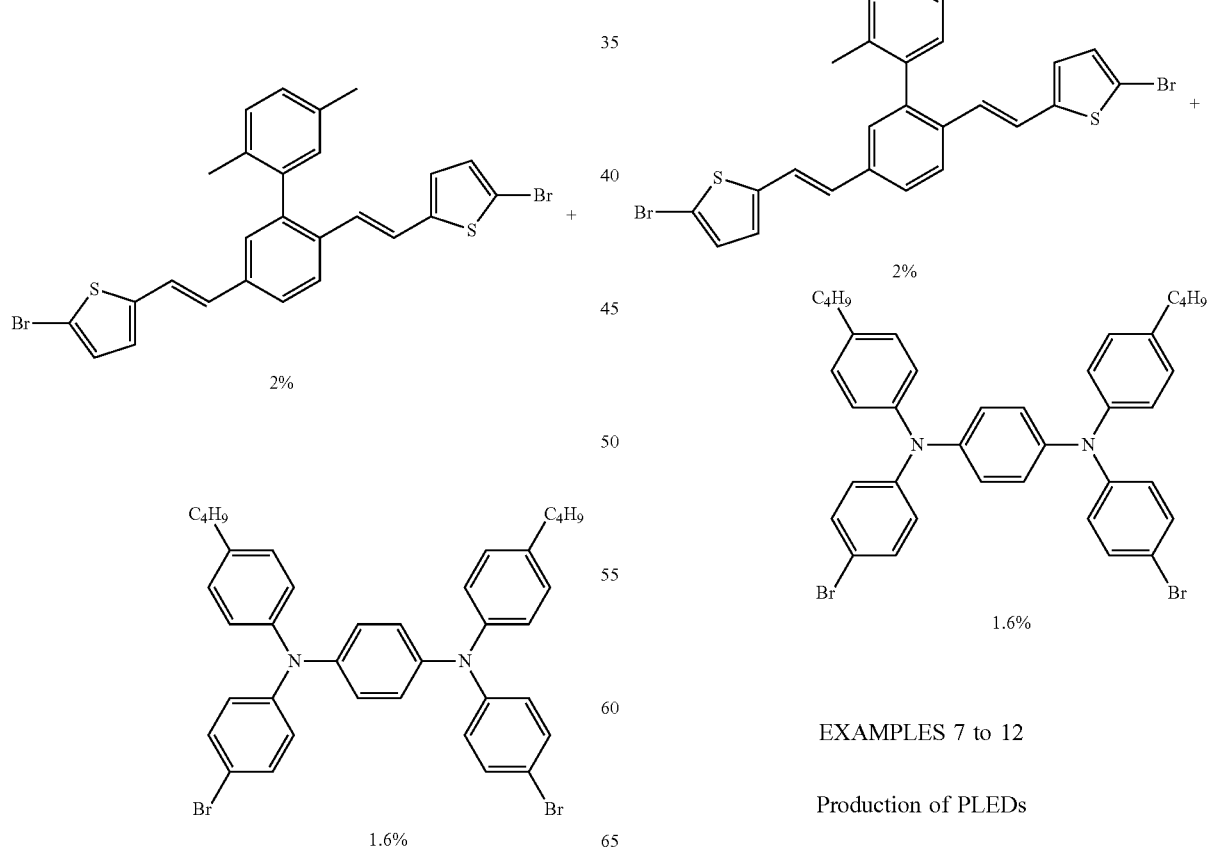
46.4%
2%
1.6%
EXAMPLES 7 to 12
Production of PLEDs
The production of a polymeric organic light-emitting diode (PLED) has already been described many times in the literature (for example in WO 2004/037887 A2). In order to explain the present invention in illustrative terms, PLEDs comprising polymers P1 to P6 according to the invention are produced by spin coating.

To this end, especially manufactured substrates from Technoprint are used in a layout designed specifically for this purpose. The ITO structure (indium tin oxide, a transparent, conductive anode) is applied to soda-lime glass by sputtering in a pattern such that 4 pixels measuring 2×2 mm arise with the cathode applied by vapour deposition at the end of the production process.

The substrates are cleaned with DI water and a detergent (Deconex 15 PF) in a clean room and then activated by UV/ozone plasma treatment. An 80 nm layer of PEDOT (PEDOT is a polythiophene derivative (Baytron P VAI 4083sp.) from H. C. Starck, Goslar, which is supplied as an aqueous dispersion) is then applied by spin coating, likewise in the clean room. The spin rate required depends on the degree of dilution and the specific spin-coater geometry (typical for 80 nm: 4500 rpm). In order to remove residual water from the layer, the substrates are dried by heating for 10 minutes at 180° C. on a hotplate. Then, under an inert-gas atmosphere (nitrogen or argon), firstly 20 nm of an interlayer (typically a hole-dominated polymer, here HIL-012 from Merck) and then 65 nm of the polymer layers are applied from toluene solutions (concentration of interlayer 5 g/l, for polymers P1 to P6 between 8 and 10 g/l). The two layers are dried by heating at 180° C. for at least 10 minutes. The Ba/Al cathode is then applied in the pattern indicated by vapour deposition through a vapour-deposition mask (high-purity metals from Aldrich, particularly barium 99.99% (Order No. 474711); vapour-deposition units from Lesker or others, typical vacuum level 5×10$^{-6}$ mbar). In order to protect, in particular, the cathode against air and atmospheric moisture, the device is finally encapsulated and then characterised.

To this end, the devices are clamped into holders manufactured specifically for the substrate size and provided with spring contacts. A photodiode with eye response filter can be placed directly on the measurement holder in order to exclude influences from extraneous light.

The voltages are typically increased from 0 to max. 20 V in 0.2 V steps and reduced again. For each measurement point, the current through the device and the photocurrent obtained are measured by the photodiode. In this way, the IUL data of the test devices are obtained. Important parameters are the maximum efficiency measured ("max. eff." in cd/A) and the voltage required for 100 cd/m$^2$.

In order, in addition, to know the colour and the precise electroluminescence spectrum of the test devices, the voltage required for 100 cd/m$^2$ is applied again after the first measurement, and the photodiode is replaced by a spectrum measurement head. This is connected to a spectrometer (Ocean Optics) by an optical fibre. The colour coordinates (CIE: Commission Internationale de l'Éclairage, standard observer from 1931) can be derived from the measured spectrum.

The results obtained on use of polymers P1 to P6 in PLEDs are shown in Table 1.

TABLE 1

| Ex. | Interlayer | Polymer | Max. eff. [cd/A] | Max. eff. [lm/W] | U @ 100 cd/m$^2$ [V] | U @ 1000 cd/m$^2$ [V] | CIE [x/y] |
|---|---|---|---|---|---|---|---|
| 7 | HIL-012 | P1 | 5.97 | 2.8 | 4.08 | 5.48 | 0.15/0.18 |
| 8 | HIL-012 | P2 | 6.24 | 2.9 | 3.96 | 5.21 | 0.15/0.18 |
| 9 | HIL-012 | P3 | 6.11 | 3.1 | 3.72 | 4.98 | 0.15/0.18 |
| 10 | HIL-012 | P4 | 17.81 | 12.7 | 3.57 | 4.55 | 0.31/0.60 |
| 11 | HIL-012 | P5 | 19.21 | 12.8 | 3.76 | 4.72 | 0.31/0.59 |
| 12 | HIL-012 | P6 | 19.04 | 13.2 | 3.32 | 4.32 | 0.31/0.60 |

The invention claimed is:

1. A polymer comprising 30 to 60 mol % of one or more structural elements of the formula (I),

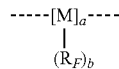

wherein

M on each occurrence, identically or differently, represents a benzene, naphthalene, anthracene, benzanthracene, benzofluorene, dibenzofluorene, cis- or trans-indenofluorene, benzindenofluorene, dibenzindenofluorene, spirobifluorene, phenanthrene, benzophenanthrene or dihydrophenanthrene derivative, where the substituents $R_F$ defined below and are identical or different on each occurrence, with the proviso that the following applies to the indices a and b:

1≤a≤10,000

1≤b≤10 and the dashed lines represent bonds to adjacent structural units, where, in addition, more than the two bonds shown may occur, and the polymer optionally comprise further identical or different structural elements M which are not substituted by partially fluorinated radicals $R_F$, with the proviso that the sum of the structural units M is between 2 and 10,000, and furthermore $R_F$ represents, identically or differently, a partially fluorinated non-aromatic substituent having 1 to 20 C atoms, which is optionally saturated or unsaturated, linear, cyclic or branched and in which one CH$_2$ groups is optionally replaced by O, S, Si(R$^2$)$_2$, BR$^2$, NR$^2$, PR$^2$, CO, C=S, C=NR$^2$, PO(R$^2$), PS(R$^2$), R$^2$C=CR$^2$, C≡C, SO, SO$_2$, O(CO)O or CONR$^2$, and R$^2$ on each occurrence, identically or differently, represents H, F or an aliphatic, aromatic and/or heteroaromatic hydrocarbon radical having 1 to 20 C atoms, in which one or more H atoms is optionally replaced by F and (i) units which are used as polymer backbone wherein the units which are used as polymer backbone are selected from 4,5-dihydropyrene derivatives, 4,5,9,10-tetrahydropyrene derivatives, fluorene derivatives, 9,9'-spirobifluorene derivatives, phenanthrene derivatives, 9,10- dihydrophenanthrene derivatives, 5,7-dihydrodibenzoxepine derivatives and cis- and trans-indenofluorene derivatives.

2. The polymer according to claim 1, wherein the structural element M represents a benzene, naphthalene, anthracene, benzanthracene, cis- or trans-indenofluorene, benzindenofluorene, dibenzindenofluorene, spirobifluorene, phenanthrene, benzophenanthrene or dihydrophenanthrene derivative.

3. The polymer according to claim 1, wherein the polymer comprises one or more structural elements M selected from one or more of the following formulae (IV) to (XXXIV):

formula (IV)
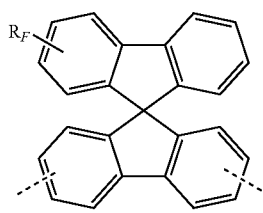

formula (V)
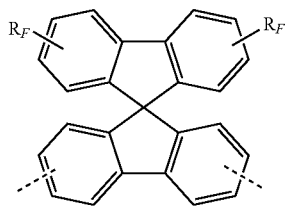

formula (VI)
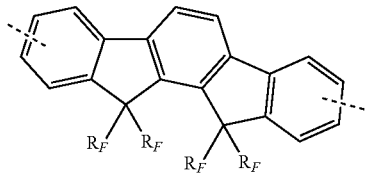

formula (VII)
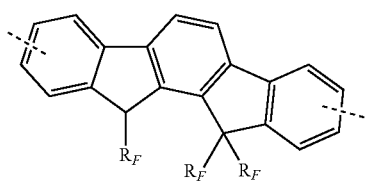

formula (VIII)
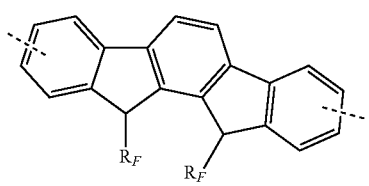

formula (IX)
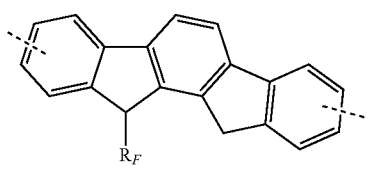

formula (X)
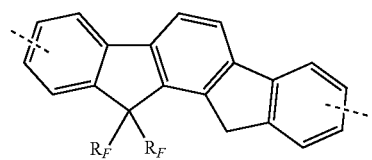

formula (XI)
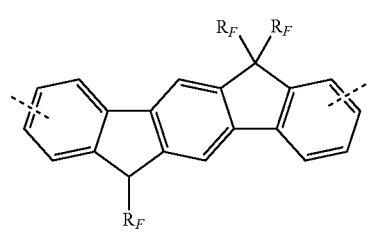

formula (XII)
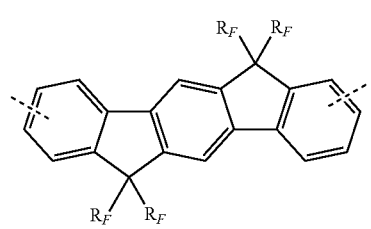

formula (XIII)
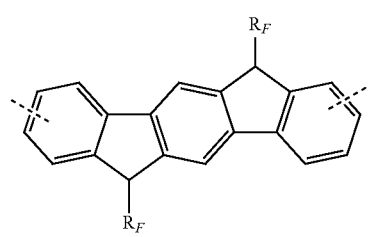

formula (XIV)
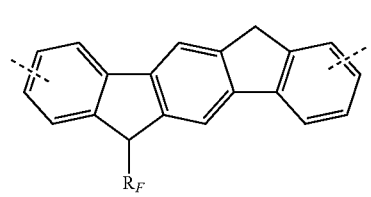

formula (XV)
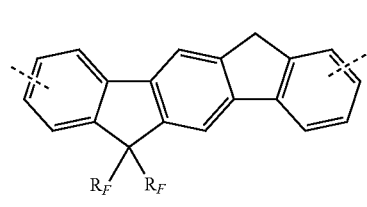

formula (XVI)
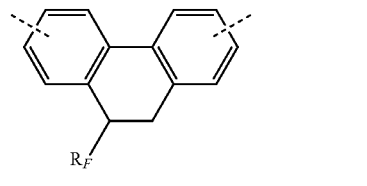

formula (XVII)
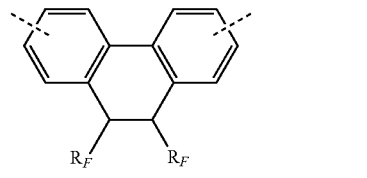

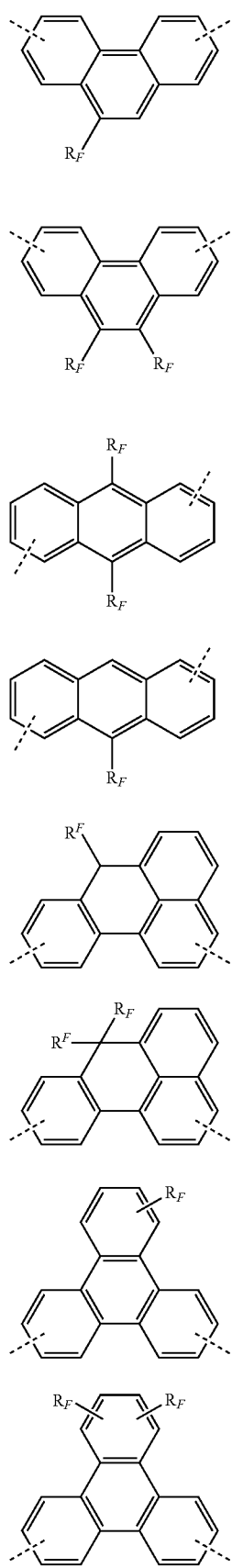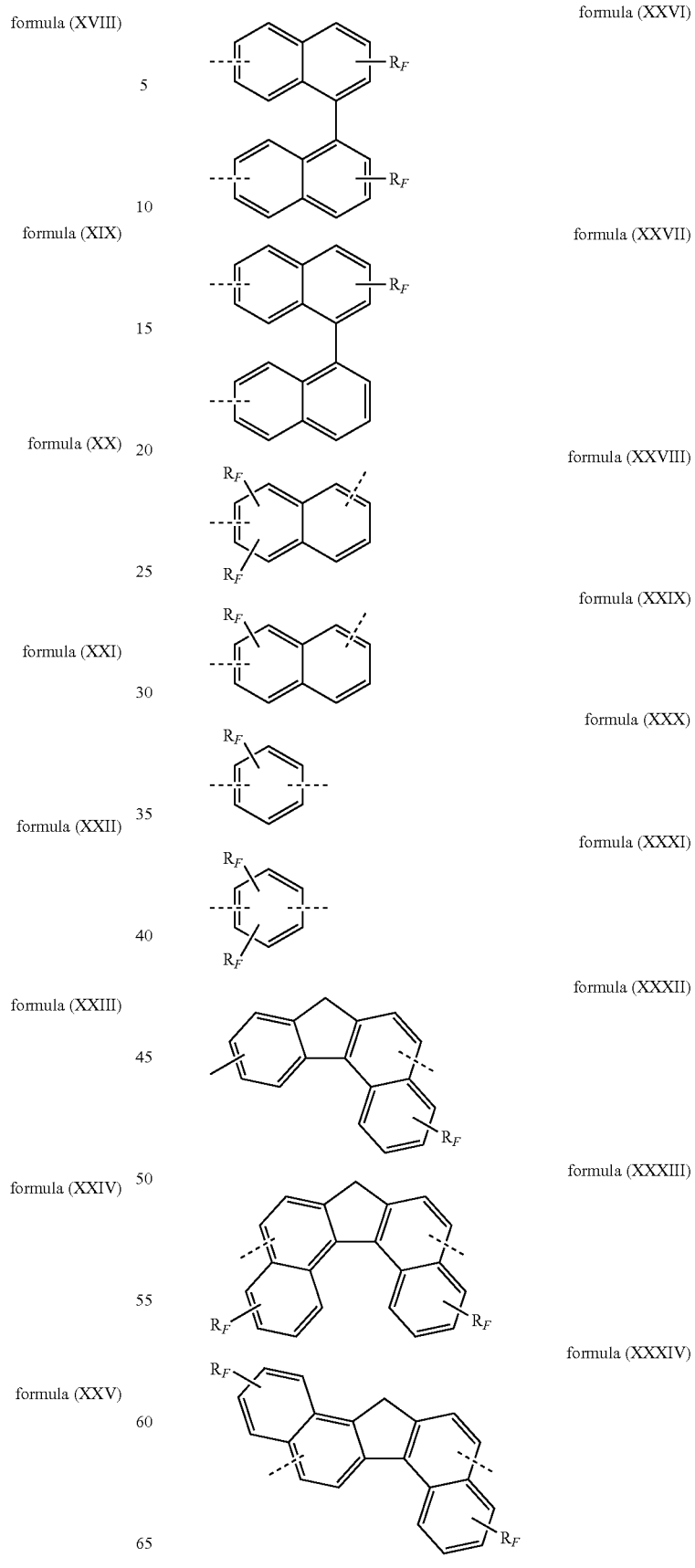

where the structural elements, as defined in claim 1, may optionally be substituted at all H-substituted positions of the skeleton instead by one or more identical or different radicals $R^1$.

4. The polymer according to claim 1, wherein $R_F$ represents a partially fluorinated saturated linear, branched or cyclic alkyl group which contains 1 to 12 C atoms and in which one $CH_2$ groups may optionally be replaced by O, S, $NR^2$, C=O or $CONR^2$.

5. The polymer according to claim 1, wherein $R_F$ comprises one or more structural elements selected from the groups —$OCF_3$, —$SCF_3$, —$N(CF_3)_2$ and terminal aliphatic trifluoromethyl.

6. The polymer according to claim 1, wherein the polymer has a molecular weight of 100,000 to 2,000,000 g/mol.

7. The polymer according to claim 1 comprising structural elements which fulfil one or more of the following functions: charge transport, charge injection, hole transport, hole injection, emission, charge blocking, or morphology, rheology or processability improvement.

8. The polymer according to claim 1, wherein the polymer has a molecular weight of 200,000 to 1,000,000 g/mol.

9. A polymer comprising
(i) 30 to 60 mol % of one or more structural elements of the formula (I),

wherein
M on each occurrence, identically or differently, represents an aromatic, heteroaromatic or aliphatically bridged aromatic ring system, which is optionally substituted by one or more radicals $R^1$, where the substituents $R_F$ and $R^1$ defined below and are identical or different on each occurrence, with the proviso that the following applies to the indices a and b:

1≤a≤10,000

1≤b≤10 and the dashed lines represent bonds to adjacent structural units, where, in addition, more than the two bonds shown may occur, and the polymer optionally comprise further identical or different structural elements M which are not substituted by partially fluorinated radicals $R_F$, with the proviso that the sum of the structural units M is between 2 and 10,000, and furthermore $R_F$ represents, identically or differently, a partially fluorinated non-aromatic substituent having 1 to 20 C atoms, which is optionally saturated or unsaturated, linear, cyclic or branched and in which one —$CH_2$ groups is optionally replaced by O, S, $Si(R^2)_2$, $BR^2, NR^2, PR^2$, CO, C=S, C=$NR^2$, $PO(R^2)$, $PS(R^2)$, $R^2C$=$CR^2$, C≡C, SO, $SO_2$, COO, O(CO)O or $CONR^2$,
and $R^1$ on each occurrence, identically or differently, represents H, F or an aliphatic, aromatic and/or heteroaromatic hydrocarbon radical having 1 to 20 C atoms, in which, in addition, one or more H atoms may be replaced by F and in which, in addition, one or more adjacent or non-adjacent $CH_2$ groups is optionally replaced by O, S, Se, Te, $Si(R^2)_2$, $Ge(R^2)_2$, $BR^2$, $NR^2$, $PR^2$, CO, C=S, C=Se, C=$NR^2$, $PO(R^2)$, $PS(R^2)$, $R^2C$=$CR^2$, C≡C, SO, $SO_2$,COO, O(CO)O or $CONR^2$, with the proviso that two or more substituents $R^1$ which are bonded to one group M or to two or more different adjacent or non-adjacent groups M optionally faun an aliphatic, unsaturated or aromatic ring system, and $R^2$ on each occurrence, identically or differently, represents H, F or an aliphatic, aromatic and/or heteroaromatic hydrocarbon radical having 1 to 20 C atoms, in which one or more H atoms is optionally replaced by F
and the polymer comprises further structural units which influence the hole-injection and/or hole-transport properties of the polymer and which are selected from the group consisting of triarylamine, benzidine, tetraaryl-paraphenylenediamine, triarylphosphine, phenothiazine, phenoxazine, dihydrophenazine, thianthrene, dibenzo-para-dioxin, phenoxathiyne, carbazole, azulene, thiophene, pyrrole and furan derivatives and (ii) 0.5 to 50 mol % of units of group 1 which influence the hole-injection and/or hole-transport properties of the polymer and/or units of group 2 which influence the electron-injection and/or electron-transport of the polymer, (iii) units which are typically used as polymer backbone, (iv) wherein the units which influence the hole-injection and/or hole-transport properties are selected from triarylamine, benzidine, tetraaryl-para-phenylenediamine, triarylphosphine, phenothiazine, phenoxazine, dihydrophenazine, thianthrene, dibenzo-para-dioxin, phenoxathiyne, carbazole, azulene, thiophene, pyrrole and furan derivatives, (v) wherein the units which influence the electron-injection and/or electron-transport of the polymer are selected from pyridine, pyrimidine, pyridazine, pyrazine, oxadiazole, quinoline, quinoxaline, anthracene, benzanthracene, pyrene, perylene, benzimidazole, triazine, ketone, phosphine oxide and phenazine derivatives, and (vi) wherein the units which are typically used as polymer backbone are selected from 4,5-dihydropyrene derivatives, 4,5,9,10-tetrahydropyrene derivatives, fluorene derivatives, 9,9'-spirobifluorene derivatives, phenanthrene derivatives, 9,10-dihydrophenanthrene derivatives, 5,7-dihydrodibenzoxepine derivatives and cis- and trans-indenofluorene derivatives.

10. The polymer according to claim 9, wherein the polymer has a molecular weight of 100,000 to 2,000,000 g/mol.

11. The polymer according to claim 9, wherein the polymer has a molecular weight of 200,000 to 1,000,000 g/mol.

12. The polymer according to claim 9, wherein the further structural units are triarylamine.

13. The polymer according to claim 9, wherein the structural element M represents an aromatic ring system having 6 to 40 C atoms.

14. A polymer comprising
(i) 30 to 60 mol % of one or more structural elements of the formula (I),

wherein

M on each occurrence, identically or differently, represents a benzene, naphthalene, anthracene, benzanthracene, benzofluorene, dibenzofluorene, cis- or trans-indenofluorene, benzindenofluorene, dibenzindenofluorene, spirobifluorene, phenanthrene, benzophenanthrene or dihydrophenanthrene derivative, where the substituents $R_F$ defined below and are identical or different on each occurrence, with the proviso that the following applies to the indices a and b:

$1 \leq a \leq 10,000$ $1 \leq b \leq 10$ and the dashed lines represent bonds to adjacent structural units, where, in addition, more than the two bonds shown may occur, and the polymer optionally comprise further identical or different structural elements M which are not substituted by partially fluorinated radicals $R_F$, with the proviso that the sum of the structural units M is between 2 and 10,000, and furthermore $R_F$ represents, identically or differently, a partially fluorinated non-aromatic substituent having 1 to 20 C atoms, which is optionally saturated or unsaturated, linear, cyclic or branched and in which one —$CH_2$ groups is optionally replaced by O, S, $Si(R^2)_2$, $BR^2$, $NR^2$, $PR^2$, CO, C=S, C=$NR^2$, $PO(R^2)$, $PS(R^2)$, $R^2C$=$CR^2$, C≡C, SO, $SO_2$, COO, O(CO)O or $CONR^2$, and $R^1$ on each occurrence, identically or differently, represents H, F or an aliphatic, aromatic and/or heteroaromatic hydrocarbon radical having 1 to 20 C atoms, in which, in addition, one or more H atoms may be replaced by F and in which, in addition, one or more adjacent or non-adjacent $CH_2$ groups is optionally replaced by O, S, Se, Te, $Si(R^2)_2$, $Ge(R^2)_2$, $BR^2$, $NR^2$,$PR^2$, CO, C=S, C=Se, C=$NR^2$,$PO(R^2)$, $PS(R^2)$, $R^2C$=$CR^2$, C≡C, SO, $SO_2$,COO, O(CO)O or $CONR^2$, with the proviso that two or more substituents $R^1$ which are bonded to one group M or to two or more different adjacent or non-adjacent groups M optionally form an aliphatic, unsaturated or aromatic ring system, and $R^2$ on each occurrence, identically or differently, represents H, F or an aliphatic, aromatic and/or heteroaromatic hydrocarbon radical having 1 to 20 C atoms, in which one or more H atoms is optionally replaced by F and (ii) 0.5 to 50 mol % of units of group 1 which influence the hole-injection and/or hole-transport properties of the polymer and/or units of group 2 which influence the electron-injection and/or electron-transport of the polymer, (iii) units which are typically used as polymer backbone, (iv) wherein the units which influence the hole-injection and/or hole-transport properties are selected from triarylamine, benzidine, tetraaryl-para-phenylenediamine, triarylphosphine, phenothiazine, phenoxazine, dihydrophenazine, thianthrene, dibenzo-para-dioxin, phenoxathiyne, carbazole, azulene, thiophene, pyrrole and furan derivatives, (v) wherein the units which influence the electron-injection and/or electron-transport of the polymer are selected from pyridine, pyrimidine, pyridazine, pyrazine, oxadiazole, quinoline, quinoxaline, anthracene, benzanthracene, pyrene, perylene, benzimidazole, triazine, ketone, phosphine oxide and phenazine derivatives, and (vi) wherein the units which are typically used as polymer backbone are selected from 4,5-dihydropyrene derivatives, 4,5,9,10-tetrahydropyrene derivatives, fluorene derivatives, 9,9'-spirobifluorene derivatives, phenanthrene derivatives, 9,10-dihydrophenanthrene derivatives, 5,7-dihydrodibenzoxepine derivatives and cis- and trans-indenofluorene derivatives.

\* \* \* \* \*